United States Patent
Corboy, Jr.

(10) Patent No.: US 12,029,741 B1
(45) Date of Patent: Jul. 9, 2024

(54) 5 BETA DIHYDROTESTOSTERONE PHARMACEUTICAL FORMULATIONS AND RELATED METHODS

(71) Applicant: Edward Dunne Corboy, Jr., Skokie, IL (US)

(72) Inventor: Edward Dunne Corboy, Jr., Skokie, IL (US)

(*) Notice: Subject to any disclaimer, the term of this patent is extended or adjusted under 35 U.S.C. 154(b) by 0 days.

(21) Appl. No.: 17/853,497

(22) Filed: Jun. 29, 2022

Related U.S. Application Data

(60) Provisional application No. 63/216,426, filed on Jun. 29, 2021.

(51) Int. Cl.
*A61K 31/568* (2006.01)
*A61K 9/00* (2006.01)
*A61K 9/06* (2006.01)

(52) U.S. Cl.
CPC .......... *A61K 31/568* (2013.01); *A61K 9/0095* (2013.01); *A61K 9/06* (2013.01); *A61K 9/0019* (2013.01)

(58) Field of Classification Search
CPC .............................. A61K 31/568; C07J 1/0022
See application file for complete search history.

(56) References Cited

PUBLICATIONS

Perusquia et al., Systemic Hypotensive Effects of Testosterone are Androgen Structure-Specific and Neuronal Nitric Oxide Synthase-Dependent, American Journal of Physiology, vol. 309, No. 2, pp. R189-R195 (Year: 2015).*

Perusquia M, Stallone JN, Do androgens play a beneficial role in the regulation of vascular tone? Nongenomic vascular effects of testosterone metabolites. Am J Physiol Heart Circ Physiol. May 2010;298(5):H1301-7. DOI: 10.1152/ajpheart.00753.2009. Epub Mar. 12, 2010. PMID: 20228257; PMCID: PMC2867446.

Perusquia M, Greenway CD, Perkins LM, Stallone JN. Systemic hypotensive effects of testosterone are androgen structure-specific and neuronal nitric oxide synthase-dependent. Am J Physiol Regul Integr Comp Physiol. Jul. 15, 2015;309(2):R189-95. DOI: 10.1152/ajpregu.00110.2015. Epub May 6, 2015. PMID: 25947172; PMCID: PMC4504958.

Swerdloff RS, Dudley RE, Page ST, Wang C, Salameh WA. Dihydrotestosterone: Biochemistry, Physiology, and Clinical Implications of Elevated Blood Levels. Endocr Rev. Jun. 1, 2017;38(3):220-254. DOI: 10.1210/er.2016-1067. PMID: 28472278; PMCID: PMC6459338.

Di Costanzo L, Drury JE, Christianson DW, Penning TM. Structure and catalytic mechanism of human steroid 5beta-reductase (AKR1D1). Mol Cell Endocrinol. Mar. 25, 2009;301(1-2):191-8. DOI: 10.1016/j.mce.2008.09.013. Epub Sep. 19, 2008. PMID: 18848863; PMCID: PMC2675190.

Rawla P., Epidemiology of Prostate Cancer. World J Oncol. Apr. 2019;10(2):63-89. DOI: 10.14740/wjon1191. Epub Apr. 20, 2019. PMID: 31068988; PMCID: PMC6497009.

Perusquia M, Espinoza J, Montaño LM, Stallone JN. Regional differences in the vasorelaxing effects of testosterone and its 5-reduced metabolites in the canine vasculature. Vascul Pharmacol. Mar.-Apr. 2012;56 (3-4):176-82. DOI: 10.1016/j.vph.2012.01.008. Epub Feb. 1, 2012. PMID: 22326440; PMCID: PMC3312741.

Glaser, R, Dimitrakakis, C. Testosterone and breast cancer prevention. Maturitas 82 (2015) 290-294. DOI: 10.1016/j.maturitas.2015.06.002. PMID: 26160683.

Nikolaos Nikolaou, Leanne Hodson, and Jeremy W. Tomlinson, The role of 5-reduction in physiology and metabolic disease: evidence from cellular, pre-clinical and human studies. Oxford Centre for Diabetes, Endocrinology and Metabolism, NIHR Oxford Biomedical Research Centre, University of Oxford, Churchill Hospital, Oxford, OX3 7LE, UK. Abstract only, 2021.

* cited by examiner

*Primary Examiner* — Brenda L Coleman
(74) *Attorney, Agent, or Firm* — McAndrews, Held & Malloy, Ltd.

(57) ABSTRACT

The present invention relates to the composition and method of use 5 Beta Dihydrotestosterone (5β-DHT) (17β-hydroxy-5β-androstan-3-one) pharmaceutical formulations used alone, or in fixed combination, with other hormones, hormone analogues, medications, health supplements, and/or genomic and nanotechnology therapeutics, using multiple drug delivery routes of administration, for the promotion of health, the prevention of illness and disease, and aesthetic disorders. and treatment of human, mammalian and animal illness and disease and health conditions, health disorders and health related pathophysiology or physiologic disorders, including, but not limited to cardiovascular disorders, endocrine disorders, prostate disorders, breast disorders, vascular disorders, oncology and cancer disorders and diseases, central nervous system disorders including dementia and cerebrovascular diseases, dermatology disorders, scalp alopecia disorders, hair biology disorders, erectile dysfunction, Peyronie's disease, as a birth control therapy, and many types of cancer related to hormone action in humans, mammals and animals.

3 Claims, 1 Drawing Sheet

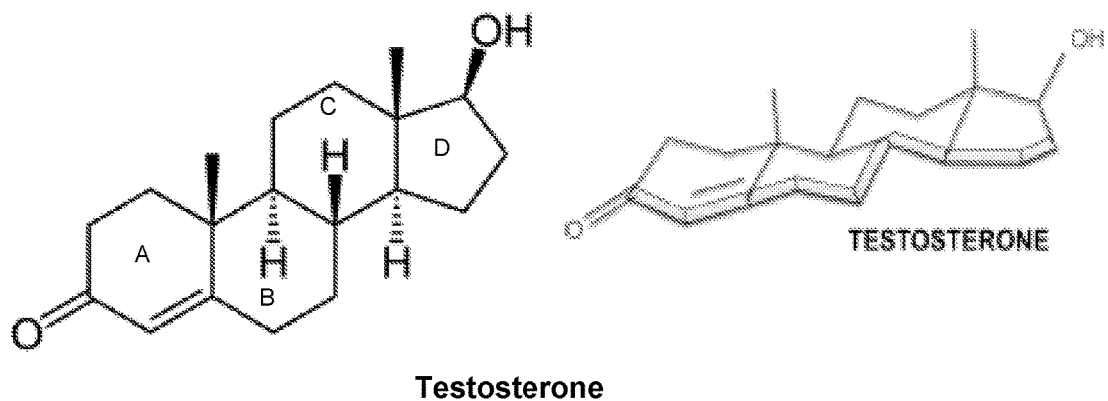
Testosterone
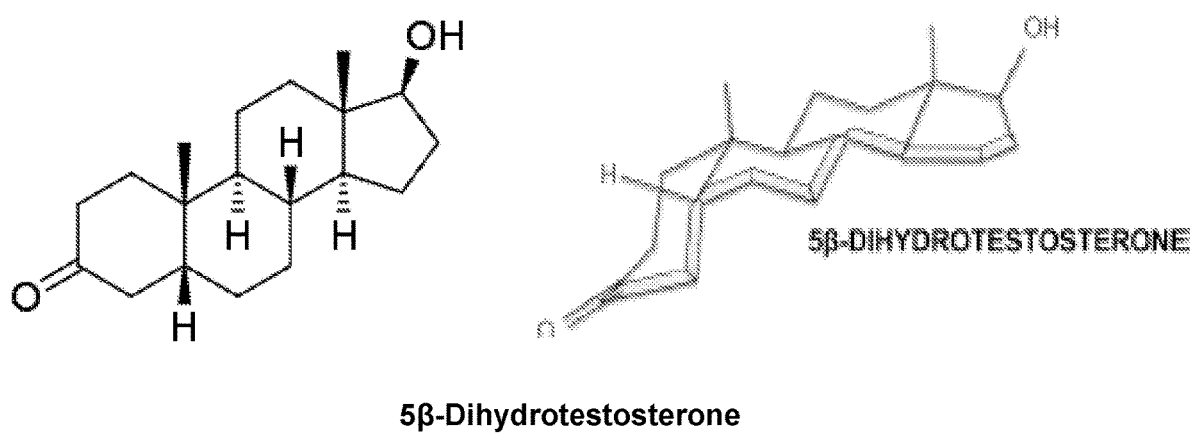
5β-Dihydrotestosterone

5 BETA DIHYDROTESTOSTERONE PHARMACEUTICAL FORMULATIONS AND RELATED METHODS

CROSS-REFERENCE TO RELATED APPLICATIONS

The application claims priority to U.S. provisional patent application Ser. No. 63/216,426, filed Jun. 29, 2021, which is hereby incorporated by reference in its entirety.

BACKGROUND

This disclosure provides solutions to a number of persistent problems relating to human health and well-being. While a number of options exist relating to androgen/hormone-based therapeutics, there remains a need for additional therapies that can provide new and useful benefits to the fields of medicine, pharmacology, cosmetology, clinical pharmacology, endocrinology, and androgen hormone therapeutics. As described in more detail below, the disclosure is directed to compositions and methods of use that comprise 5 Beta Dihydrotestosterone (5β-DHT) (17β-hydroxy-5β-androstan-3-one), and including pharmaceutical formulations thereof.

SUMMARY

The disclosure relates to a composition and related methods of use comprising 5 Beta Dihydrotestosterone (5β-DHT) (17β-hydroxy-5β-androstan-3-one) as pharmaceutical formulations used alone, or in fixed combination, with other hormones, hormone analogues, medications, health supplements, and/or genomic and nanotechnology therapeutics, using multiple drug delivery routes of administration, for the promotion of health, the prevention of illness and disease, the prevention and treatment of aesthetic disorders and treatment of human, mammalian and animal illness and diseases, health conditions, health disorders, inborn rare genetic and epigenetic disorders of hormone and hormone receptors as described by the U.S. National Institute of Health Genetic and Rare Diseases ("GARD") website pages, of and health related pathophysiology or physiologic disorders, including, but not limited to, internal medicine disorders, cardiovascular disorders, endocrine disorders, prostate disorders, breast disorders, vascular disorders, oncology and cancer disorders and diseases, central nervous system disorders including dementia and cerebrovascular diseases, dermatology disorders, scalp alopecia disorders, hair biology disorders, erectile dysfunction, Peyronie's disease, as a birth control therapy, and many types of cancer related to hormone action in humans, mammals and animals.

The methods and therapeutic use of 5β-DHT offers many novel, nonobvious and useful pharmaceutical therapeutic benefits (when used alone or in combination with other hormones, hormone analogues, hormone metabolites, 5 alpha reductase inhibitors, androgen receptor blocker medications, other hormone therapies, other medications that enhance vasodilation of the vasculature (arteries, arterioles, and other vascular structures in the body) and vasodilation of blood vessels and that will enhance the blood flow and vascular supply to tissues and organs of the body, including, but not limited to, the skin, subcutaneous tissues, prostate gland, hair follicles, hair follicles on the scalp, and to the heart, lungs, eyes, skin, central and peripheral nervous system, musculoskeletal systems, brain, kidneys, penis, clitoris, and/or genomic therapeutics for the promotion of health, the prevention illness and/or disease, and treatment of human, mammalian and animal health conditions, disorders, illness and diseases.

There are a great number of health issues, (e.g., health disorders, diseases, illnesses, conditions and issues relating to aesthetics, hair biology, hair loss disorders (alopecia) and many others) that have long-felt but unmet needs for improved pharmaceutical therapies and innovative treatments by health professionals, scientists and the general public.

Currently, there remain many long-standing unmet needs and for many health problems, health disorders, diseases, health disorders, aesthetic disorders and all too common health related problems for human beings, mammals and animal health that are in great need to novel, useful and nonobvious pharmaceutical therapies and treatments to prevent, treat and provide benefits for a wide range of health disorders in humans, mammals, and animals that the best and leading experts in medicine, pharmacy, clinical pharmacology, science and pharmaceutical therapeutics have yet to discover or consider as novel, nonobvious and useful pharmaceutical therapies that may offer many potential important benefits to a host of human beings, mammals and animals.

BRIEF DESCRIPTION OF THE DRAWINGS

The FIGURE (FIG. 1) depicts the chemical structures and stereochemistry of Testosterone and 5β-dihydrotestosterone.

DETAILED DESCRIPTION

Testosterone, 5α-dihydrotestosterone and 5β-dihydrotestosterone are steroid hormones and part of the androgen steroid hormone family of hormones. A steroid (or steroid hormone) is a biologically active organic compound with a chemical structure composed of four (4) rings arranged in 3 dimensional stereoisomer specific molecular configurations. Steroids have many important biological functions and effects on physiology including, but not limited to, as important components of cell membranes which alter membrane fluidity; and as signaling molecules. Hundreds of steroids are found in plants, animals and fungi. All steroids are produced and manufactured in cells from the sterols lanosterol (opisthokonts) or cycloartenol (plants). Lanosterol and cycloartenol are derived from the cyclization of the triterpene squalene.

The steroid core structure is typically composed of seventeen (17) carbon atoms, bonded in four (4) "fused" rings: three (3) six-member cyclohexane rings (rings A, B and C in the first illustration) and one (1) five-member cyclopentane ring (the D ring). Steroids vary by the functional groups attached to this four-ring core and by the oxidation state of the rings. Sterols are forms of steroids with a hydroxy group at position three and a skeleton derived from cholestane. Steroids can also be more radically modified, such as by changes to the ring structure, for example, cutting one of the rings. Cutting Ring B produces secosteroids one of which is vitamin D3.

5 Beta Dihydrotestosterone (5β-Dihydrotestosterone (5β-DHT)), also known as 5β-androstan-17β-ol-3-one or as etiocholan-17β-ol-3-one, is an etiocholane (5β-androstane) steroid as well as an inactive metabolite of testosterone formed by 5β-reductase in the liver and bone marrow and an intermediate in the formation of 3α,5β-androstanediol and 3β,5β-androstanediol (by 3α- and 3β-hydroxysteroid dehydrogenase) and, from them, respectively, etiocholanolone and epietiocholanolone (by 17β-hydroxysteroid dehydrogenase). Unlike its isomer, 5α-dihydrotestosterone (5α-DHT or simply DHT), 5β-DHT either does not bind to or binds only very weakly to the androgen receptor. 5β-DHT is notable among metabolites of testosterone in that, due to the fusion of the A and B rings (of the steroid 4 ring structure) in the cis orientation, where that A ring is at an approximate 90 degree angle to the B Ring of the androgen ring structure. Some suggest the fusion angle of the and A and B rings of 5β-DHT is closer to 67 degrees. This extremely angular molecular structure of 5β-DHT when viewed as a 3 dimensional androgen hormone, and this could be related to its lack of androgenic activity, and it weak binding to androgen receptors (AR), that is in stark contrast to the 5α-DHT isomer. 5β-DHT, unlike 5α-DHT, is also inactive in terms of neurosteroid activity, although its metabolite, etiocholanolone, does possess such activity.

It is known that A:B Ring Fusion in the dihydrotestosterone isomer molecules (alpha or beta isomers) may be cis to trans. When the A:B ring fusion is trans (as in 5α-DHT), then the A ring and the B ring are more planer (flat) compared to the acute angulation with the A:B ring fusions in 5β-DHT that is cis. Five alpha reduction of testosterone (T) leads to the more planer (flat) 5α-DHT isomer that is a very potent androgen with the strongest binding kinetics of any naturally occurring, endogenously produced androgen hormone in humans, mammals and animals. The transisomer of DHT is the easiest to describe because the fusion of the A & B rings creates a rigid, roughly planar, structure made up of two chair conformations.

In stark contrast, the five beta reduction of testosterone (T) leads to the more angular 5β-DHT isomer at the A:B Ring junction, and 5β-DHT isomer is a very weak androgen with very minimal binding kinetics to the androgen receptor (AR) compared to testosterone (T) and 5α-DHT (naturally occurring, endogenously produced androgen hormones in humans, mammals and animals).

The major synthetic pathway of 5α-DHT formation and metabolism is that testosterone (T) is synthesized in men by the testis and in women either directly by the adrenals and ovaries, or by peripheral conversion of androstenedione. Testosterone is then irreversibly converted to 5α-DHT by the NADPH-dependent enzyme 5a reductase, or aromatized to the potent oestrogen 17β-oestradiol.

The major synthetic pathway of 5β-DHT formation and metabolism is that testosterone (T) is synthesized in men by the testis and in women either directly by the adrenals and ovaries, or by peripheral conversion of androstenedione. Testosterone is then irreversibly converted to 5β-DHT by the NADPH-dependent enzyme 5β-reductase, or aromatized to the potent oestrogen 17β-oestradiol.

Steroids

The Tetracyclic Chemistry Ring Structure Common to Steroid Hormones

There are four rings in a steroid skeleton and hence there are three fusion points. A/B, B/C and C/D rings share two carbons each (fusion). Every fusion center can either be cis- or trans-fused.

The accepted chemistry and pharmacology for numbering of each position of the 4 ring, steroid ring structure essentially follows a uniform pattern except for the methyls, whereas A/B rings have carbon 19, C/D rings have carbon 18. Cholesterol is an important member of the cholestane series of steroids.

Steroids are widely distributed in animals, where they are associated with a number of physiological processes. The generic steroid structure has seven chiral stereocenters (carbons 5, 8, 9, 10, 13, 14 & 17), which means that it may have as many as 128 stereoisomers. With the exception of C-5, natural steroids generally have a single common configuration. The important class of lipids called steroids are actually metabolic derivatives of terpenes, but they are customarily treated as a separate group. Steroids may be recognized by their tetracyclic skeleton, consisting of three (3) fused six-membered rings and one (1) five-membered ring, as shown below. The four rings are designated A, B, C & D as noted, and the peculiar numbering of the ring carbon atoms (shown in red) is the result of an earlier misassignment of the structure.

The substituents that are attached the core steroid four ring structure are designated by R are often alkyl groups, but may also have functionality. The R group at the A:B ring fusion is most commonly methyl or hydrogen, that at the C:D fusion is usually methyl. The substituent at C-17 varies considerably, and is usually larger than methyl if it is not a functional group. The most common locations of functional groups are C-3, C-4, C-7, C-11, C-12 & C-17. Ring A is sometimes aromatic. Since a number of tetracyclic triterpenes also have this tetracyclic structure, it cannot be considered a unique identifier.

The stereochemical conformation of a steroid, may be illustrated using an adequate wedge-and-broken line structure, in addition, steroid hormone chemistry illustrations and determine whether the ring substituents in such a compound occupy axial or equatorial positions.

The paper by Nikolaou, et al., provides discussion regarding the enzyme, 5 Beta Reductase (5β-reductase (5βR) (Nikolaos Nikolaou, Leanne Hodson, and Jeremy W. Tomlinson, "The role of 5-reduction in physiology and metabolic disease: evidence from cellular, pre-clinical and human studies" Oxford Centre for Diabetes, Endocrinology and Metabolism, NIHR Oxford Biomedical Research Centre, University of Oxford, Churchill Hospital, Oxford, OX3 7LE, UK. Notably it characterizes 5βR as a member of the aldo-keto-reductase (AKR) superfamily 1 of enzymes that utilizes NADPH to catalyze a stereospecific irreversible double bond reduction between the 4th and the 5th carbon of the A-ring of steroids, and can generate all 5β-reduced dihydrosteroid metabolites for C19-C27 steroids.

5 Alpha Dihydrotestosterone (5α-dihydrotestosterone, 5α-DHT)

Some experts in medicine, endocrinology and pharmacology have referred to 5 Alpha Dihydrotestosterone (5α-dihydrotestosterone, 5α-DHT) as a prostate sparing androgen when compared to testosterone. See, e.g., Swerdloff R S, et al 2017.

In this disclosure, 5 Beta DHT (5β-DHT) is demonstrated to be a useful prostate sparring androgen or "prostate protective androgen" because of its very weak binding to the androgen receptor (AR) that is significantly lower than that of 5 Alpha DHT isomer (5α-DHT) and also significantly less than that of testosterone (T). This invention offers novel advantages of 5 Beta DHT (5β-DHT) for the treatment of a host of diseases, health disorders, and health related conditions, and aesthetic disorders and 5β-DHT potent vasodilation physiological effects on the vasculature. In addition, 5β-DHT lacks any significant binding to the AR, and has reported significantly fewer androgenic effects compared to testosterone (T) and 5α-DHT, and this may allow for 5β-DHT to provide novel, nonobvious and useful methods of use, in various formulations, delivered in many drug delivery approaches, including topical application to the skin, parenteral administration, infusion pump delivery, implantable infusion pump, indwelling catheters, and implantable slow release pellets or mass like structures (that may have nanotechnology designs to promote steady delivery of therapeutic 5β-DHT to targeted tissues).

5 Alpha Dihydrotestosterone (5 Alpha DHT, 5α-dihydrotestosterone, 5α-DHT, androstanolone or stanolone) is an endogenously produced androgen sex steroid hormone in humans, mammals and animals. The enzyme 5α-reductase catalyzes the formation of 5α-DHT from testosterone in certain tissues that have both the proper genetics and epigenetics that regulate the cell biology and molecular biology of individual cells that make up tissues, organs and well described tissues that make up organ systems, including (but not limited to) the prostate gland, seminal vesicles, epididymides, skin, hair follicles, liver, and brain. This enzyme mediates reduction of the C4-5 double bond of testosterone and in so doing metabolized testosterone into 5α-dihydrotestosterone (5α-DHT). Relative to testosterone (T), 5α-DHT is considerably more potent as an agonist of the androgen receptor (AR) and this is related to the binding affinity of the 5α-DHT and 5α-DHT dimer complexes to the AR as well as the longer 5α-DHT receptor binding kinetics and duration of binding to the AR as compared to testosterone (T). In addition to its role as a naturally produced hormone in humans, mammals and animals, topical pharmaceutical formulations of 5α-DHT has been used as a medication in countries that include France and Belgium since the early 1980's, for instance in the treatment of adult men with hypogonadism (below normal serum testosterone levels in men who often have symptoms recognized by physicians as related to below normal or low normal levels of total serum testosterone or free serum testosterone. A topical formulation of 5α-DHT is sold by Besins Healthcare and marketed under the brand name, Andractim® 2.5% 5α-DHT Gel. The Besins Healthcare company has created a formulation of 5α-DHT that is a 0.7% 5α-DHT Gel. The Besins Healthcare Company, or prior companies owed by the Besins Family over the past 50 to 100 years have sponsored research and research partnerships with companies including Unimed Pharmaceuticals of Buffalo Grove, IL in the 1990's and early 2000's years and such studies have assessed the clinical use of 5α-DHT topical hydroalcoholic gel formulations in the treatment of HIV Associated Muscle Wasting Disorders in the U.S. and perhaps outside the U.S. in the 1990's, and also assessed the use of 5α-DHT topical hydroalcoholic gel formulations in the treatment of cancer cachexia wasting disorders in the U.S. and perhaps other countries in the 1990's. Additional studies of 5α-DHT topical hydroalcoholic gel formulations have been clinical studies in the U.S. with regard to changes of prostate health status in multicenter studies in the U.S. In addition, excellent studies has been performed in the U.S. comparing 5α-DHT topical hydroalcoholic gel formulations of 2.5% v. 0.7% to placebo in human clinical studies assessing pharmacokinetics at the Harbor UCLA Medical Center. This research has been published in the medical literature and is most useful.

5α-DHT is biologically important for sexual differentiation of the male genitalia during embryogenesis, maturation of the penis and scrotum at puberty, growth of facial, body, and pubic hair, and development and maintenance of the prostate gland and seminal vesicles. 5α-DHT is produced from the less potent testosterone by the enzyme 5α-reductase in select tissues, and is the primary androgen in the genitals, prostate gland, seminal vesicles, skin, and hair follicles. 5α-DHT signals mainly in an intracrine and paracrine manner in the tissues in which it is produced, playing only a minor role, if any, as a circulating endocrine hormone. Circulating serum levels of 5α-DHT are 1/10th and 1/20th those of testosterone in terms of total and free concentrations, respectively, whereas local 5α-DHT levels may be up to 10 times those of testosterone in tissues with high 5α-reductase expression such as the prostate gland. In addition, unlike testosterone, 5α-DHT is inactivated by 3α-hydroxysteroid dehydrogenase (3α-HSD) into the very weak androgen 3α-androstanediol in various tissues such as muscle, adipose, and liver among others, and in relation to this, 5α-DHT has been reported to be a very poor anabolic agent in muscle tissues when administered exogenously as a medication because is it rapidly metabolized in muscle tissue.

In addition to well recognized and accepted important biological functions in humans, mammals and animals, 5α-DHT also plays an important causative role in a number of androgen-dependent conditions including hair conditions like hirsutism in women (excessive facial/body hair growth) and pattern hair loss on the scalp (androgenic alopecia or pattern baldness) and prostate diseases such as benign prostatic hyperplasia (BPH) and prostate cancer. 5α-Reductase inhibitors, which prevent 5α-DHT synthesis, are effective in the prevention and treatment of these conditions. Additionally, 5α-DHT may play a function in skeletal muscle amino acid transporter recruitment and function.

Metabolites of 5α-DHT have been found to act as neurosteroids with their own AR-independent biological activity. 3α-Androstanediol is a potent positive allosteric modulator of the $GABA_A$ receptor, while 3β-androstanediol is a potent and selective agonist of the estrogen receptor (ER) subtype ERs. These metabolites may play important roles in the central effects of 5α-DHT and by extension testosterone, including their antidepressant, anxiolytic, rewarding/hedonic, anti-stress, and pro-cognitive effects.

5 Beta Dihydrotestosterone (5β-dihydrotestosterone, 5β-DHT)

5 Beta Dihydrotestosterone (5β-dihydrotestosterone, 5β-DHT) is an endogenously produced androgen sex steroid and hormone in humans, mammals and animals. The enzyme 5β-reductase catalyzes the formation of 5β-DHT from testosterone in certain tissues and anatomic structures of the body, including but not limited to, the liver, the brain, the prostate gland, seminal vesicles, epididymides, skin, hair follicles, liver, and brain. This enzyme mediates 5 Beta reduction of the C4-5 double bond of testosterone. Relative to testosterone, 5β-DHT is considerably less potent as an agonist hormone that binds to the androgen receptor (AR). In fact, 5β-DHT may have approximately 1/190th the binding affinity to the androgen receptor (AR) as compared to testosterone. It is clear that 5 Beta DHT is a highly distinct isomer of dihydrotestosterone compared to 5 Alpha Dihydrotestosterone (5α-DHT). As disclosed herein, the unique hormone chemistry and pharmacological activities of (5β-DHT) may provide for heretofore unsuspected novel, non-obvious and useful therapeutic benefits for the prevention and treatment of disease, health disorders, illness, health conditions, aesthetic conditions and health related disorders in humans, mammals and animals.

Limited therapeutic uses of 5 Beta Dihydrotestosterone have been investigated and there is prior data that raises issues of potential drug-drug interactions with anticoagulant medications. To achieve a successful formulation, it is useful to assess the cytochrome P450 enzyme systems, and most common cytochrome P450 variations in human populations, mammals, and animal populations. Specifically, 5 Beta-dihydrotestosterone may increase the anticoagulant activities of Bemiparin, Betrixaban, Bivalirudin, Cangrelor or Dabigatran.

Unlike 5α-DHT, 5β-DHT has not been used as a medication that has received U.S FDA approval for any formal indications for use in human beings, and there are no known products that contain 5 Beta DHT (5β-DHT) formulations used alone, or in fixed combination, with other hormones, hormone analogues, medications, health supplements, and/or genomic and nanotechnology therapeutics, using multiple drug delivery routes of administration, for the promotion of health, the prevention of illness and disease, the prevention and treatment of aesthetic disorders and treatment of human, mammalian and animal illness and diseases, health conditions, health disorders, inborn rare genetic and epigenetic disorders of hormone and hormone receptors as described by the U.S. National Institute of Health Genetic and Rare Diseases ("GARD") website pages, of and health related pathophysiology or physiologic disorders, including, but not limited to internal medicine disorders, cardiovascular disorders, endocrine disorders, prostate disorders, breast disorders, vascular disorders, oncology and cancer disorders and diseases, central nervous system disorders including dementia and cerebrovascular diseases, dermatology disorders, scalp alopecia disorders, hair biology disorders, erectile dysfunction, Peyronie's disease, birth control therapy, and many types of cancer related to hormone action in humans, mammals and animals.

5α-Reductase Inhibitors

Disclosed herein is 5 Beta DHT (5β-DHT), as a novel, nonobvious and useful therapy to be used in conjunction with one or more 5α-Reductase inhibitors, Finasteride, Dutasteride, and MK-386 for the treatment of many diseases, disorders, health conditions and aesthetic disorders. The 5α-Reductase inhibitors, Finasteride, Dutasteride, and MK-386 are important compounds. 5α-Reductase inhibitors like finasteride and dutasteride inhibit 5α-reductase type II and/or other isoforms and are able to decrease circulating DHT levels by 65 to 98% depending on the 5α-reductase inhibitor in question. As such, similarly to the case of 5α-reductase type II deficiency, they provide useful insights in the elucidation of the biological functions of DHT. 5α-Reductase inhibitors were developed and are used primarily for the treatment of BPH. The drugs are able to significantly reduce the size of the prostate gland and to alleviate symptoms of the condition. Long-term treatment with 5α-reductase inhibitors is also able to significantly reduce the overall risk of prostate cancer, although a simultaneous small increase in the risk of certain high-grade tumors has been observed. In addition to prostate diseases, 5α-reductase inhibitors have subsequently been developed and introduced for the treatment of pattern hair loss in men. They are able to prevent further progression of hair loss in most men with the condition and to produce some recovery of hair in about two-thirds of men. 5α-Reductase inhibitors seem to be less effective for pattern hair loss in women on the other hand, although they do still show some effectiveness. Aside from pattern hair loss, the drugs are also useful in the treatment of hirsutism and can greatly reduce facial and body hair growth in women with the condition.

5α-Reductase inhibitors are overall well tolerated and show a low incidence of adverse effects. Sexual dysfunction, including erectile dysfunction, loss of libido, and reduced ejaculate volume, may occur in 3.4 to 15.8% of men treated with finasteride or dutasteride. A small increase in the risk of affective symptoms including depression, anxiety, and self-harm may be seen. Both the sexual dysfunction and affective symptoms may be due partially or fully to prevention of the synthesis of neurosteroids like allopregnanolone rather necessarily than due to inhibition of 5α-DHT production. A very small risk of gynecomastia has been associated with 5α-reductase inhibitors (1.2 to 3.5%). Based on reports of 5α-reductase type II deficiency in males and the effectiveness of 5α-reductase inhibitors for hirsutism in women, reduced body and/or facial hair growth is a likely potential side effect of these drugs in men. There are very few studies evaluating the side effects of 5α-reductase inhibitors in women. However, due to the known role of 5α-DHT in human, mammal and animal embryogenesis and male sexual differentiation, 5α-reductase inhibitors may cause birth defects such as ambiguous genitalia in the male fetuses of pregnant women. As such, they are not used in women during pregnancy.

The differences between 5 Alpha Dihydrotestosterone (5α-DHT) and 5 Beta Dihydrotestosterone (5β-DHT) are clear. See, e.g., Perusquía M, Stallone J N., "Do androgens play a beneficial role in the regulation of vascular tone? Nongenomic vascular effects of testosterone metabolites." Am J Physiol Heart Circ Physiol. 2010 May;298(5):H1301-7. doi: 10.1152/ajpheart.00753.2009. Epub 2010 Mar. 12. PMID: 20228257; PMCID: PMC2867446. FIG. 1 of the paper refers to genomic and nongenomic mechanisms of action of androgens in the vascular smooth muscle (VSM) cell and the recognized differences between Tes, 5α-DHT, and 5β-DHT and how the differences in chemical structures may impact activities.

In one embodiment, novel, nonobvious and useful opportunities to employ compositions and method of use via a recognized drug delivery routes to delivery 5 Beta Dihydrotestosterone (5β-DHT) (17β-hydroxy-5β-androstan-3-one) pharmaceutical formulations used alone, or in fixed combination, with other hormones, hormone analogues, medications, health supplements, and/or genomic and nanotechnology therapeutics, using multiple drug delivery routes of administration, for the promotion of health, the prevention of illness and disease, the prevention and treatment of aesthetic disorders and treatment of human, mammalian and animal illness and diseases, health conditions, health disorders, inborn rare genetic and epigenetic disorders of hormone and hormone receptors as described by the U.S. National Institute of Health Genetic and Rare Diseases ("GARD") website pages, of and health related pathophysiology or physiologic disorders, including, but not limited to internal medicine disorders, cardiovascular disorders, endocrine disorders, prostate disorders, breast disorders, vascular disorders, oncology and cancer disorders and diseases, central nervous system disorders including dementia and cerebrovascular diseases, dermatology disorders, scalp alopecia disorders, hair biology disorders, erectile dysfunction, Peyronie's disease, birth control therapy, and many types of cancer related to hormone action in humans, mammals and animals.

It is generally accepted that 5 Alpha DHT (5α-DHT) is not converted or metabolized back to testosterone. Nor is it metabolized to estradiol by the enzyme aromatase.

Androgen Hormones and Vasorelaxation of Vascular Vessels

Some studies show that 5alpha-DHT is general less efficacious than testosterone as a vasodilator, while 5beta-DHT is more efficacious and/or potent than testosterone as a vasodilator, but the differences that androgens have on blood pressure in vivo is still unclear. See, e.g., Perusquía M, Stallone J N., above, and Stallone & Perusquia, "Systemic hypotensive effects of testosterone are androgen structure-specific and neuronal nitric oxide synthase-dependent" Am J Physiol Regul Integr Comp Physiol. 2015 Jul. 15; 309(2): R189-R195 (e.g., FIG. 6).

Human Steroid 5β-reductase (aldo-keto reductase (AKR) 1D1) Enzyme

A review of the Human steroid 5β-reductase (aldo-keto reductase (AKR) 1D1) enzyme is provided by DiCostanzo, L., et al., ((Di Costanzo L, Drury J E, Christianson D W, Penning T M. Structure and catalytic mechanism of human steroid 5beta-reductase (AKR1D1). Mol Cell Endocrinol. 2009 Mar. 25; 301(1-2):191-8. doi: 10.1016/j.mce.2008.09.013. Epub 2008 Sep. 19. PMID: 18848863; PMCID: PMC2675190) which discusses human steroid 5β-reductase (aldo-keto reductase (AKR) 1D1) and its role in catalyzing reduction of Δ4-ene double bonds in steroid hormones and bile acid precursors.

The Delta 4-3-Ketosterold Chemical Structure Functional Unit

With regard to testosterone and its metabolism, the delta 4-3 ketosteroid functionality (Δ4-3-ketosteroid functionality) is most important. This is true for all circulating steroid hormones in humans, except estrogens. The first step in their metabolism involves the reduction of the Δ4-ene to produce either 5α-dihydro- or 5β-dihydrosteroids in reactions catalyzed by steroid 5α-reductase or 5β-reductase, respectively (Tomkins, 1956).

Without being limited by mechanism, the steroid A/B ring junction 3 dimensional stereochemistry and its molecular structure which adopts a cis-A/B Ring or trans-A/B Ring β-configuration may play a key aspect in its activity as this relates to the 5a reduction of testosterone to 5α-DHT or the 5p reduction to 5β-DHT having a cis-A/B or β-configuration.

Δ4-3-Ketosteroid 5β-reductase is a soluble monomeric NADPH dependent enzyme and a member of the aldo-keto reductase (AKR) superfamily, and in humans is designated AKR1D1 (Kondo et al., 1994; Jez et al., 1997). In utilizing NADPH as the hydride donor, the enzymatic reaction introduces a 90° bend at the steroid A/B ring junction, which adopts a cis-A/B or β-configuration (Berseus, 1967; Okuda and Okuda, 1984; Onishi et al., 1991). This reaction is unique in steroid enzymology since the configuration of the product is difficult to achieve by synthetic methods. This change in steroid configuration is essential to establish the emulsifying properties of bile acids. In this regard AKR1D1 catalyzes the pivotal reduction of Δ4-cholesten-7α-ol-3-one and Δ4-cholesten-7α,12α-diol-3-one to yield 5β-cholestan-7α-ol-3-one and 5β-cholestane-7α,12α-diol-3-one, respectively on route to the primary bile acids, chenodeoxycholic and cholic acid (Russell, 2003; Russell and Setchell, 1992).

Based on available data on AKRs much can be inferred about the structure-function of AKR1D1. As an AKR enzyme it is predicted to have an (α/β)8-barrel fold, the cofactor binding site is likely conserved and the stereochemistry of hydride transfer is predicted to be 4-pro-R (Jez et al., 1997). Unlike other AKRs that catalyze the reduction of carbonyls, the catalytic tetrad is altered. The conserved AKR tetrad consists of Tyr, Lys, Asp, and His, where Tyr acts as the general acid/base (Grimshaw et al., 1995; Schlegel et al., 1998). However, in AKR1D1 the His is substituted with a Glu. The most thoroughly characterized steroid hormone transforming AKR is the rat 3α-hydroxysteroid dehydrogenase (AKR1C9), where mutation of the conserved His to Glu to yield the H117E mutant introduced steroid 5β-reductase activity into the enzyme when none previously existed (Jez and Penning, 1998). Although these studies confirm the importance of the H117E substitution for steroid double bond reduction, without a crystal structure it is difficult to assign a precise role for the Glu residue.

There are a large number of health issues that, in part, include disorders of the prostate gland in male humans, mammals and animals. These disorders, conditions, or diseases associated with the prostate include but are not limited to benign prostate hyperplasia (BPH) and also prostate cancers, prostate carcinomas, metastatic prostate cancer, and prostate cancer, castration resident prostate cancers that are refractory to management and treatment using anti-androgen pharmaceutical and also other therapies including castration.

Discussion of 5 Alpha Dihydrotestosterone

With respect to 5α-DHT the well established convention by medicine experts, endocrinologists, pharmacists and scientists is to use the term "DHT" when referring to 5α-DHT.

Dihydrotestosterone (DHT, 5α-dihydrotestosterone, 5α-DHT, androstanolone or stanolone) is an endogenous androgen sex steroid and hormone, catalyzed in a reaction by the enzyme 5α-reductase catalyzes from testosterone in certain tissues including the prostate gland, seminal vesicles, epididymides, skin, hair follicles, liver, and brain. This enzyme mediates reduction of the C4-5 double bond of testosterone. Relative to testosterone, 5α-DHT is considerably more potent as an agonist of the androgen receptor (AR).

In addition to its role as a natural hormone, 5α-DHT has been used as a medication, for instance in the treatment of low testosterone levels in men; for information on DHT as a medication It has an affinity (Kd) of 0.25 to 0.5 nM for the human AR, which is about 2- to 3-fold higher than that of testosterone (Kd=0.4 to 1.0 nM) and 15-30 times higher than that of adrenal androgens. In addition, the dissociation rate of 5α-DHT from the AR is 5-fold slower than that of testosterone. The EC50 of 5α-DHT for activation of the AR is 0.13 nM, which is about 5-fold stronger than that of testosterone (EC50=0.66 nM). In bioassays, 5α-DHT has been found to be 2.5- to 10-fold more potent than testosterone.

The elimination half-life of 5α-DHT in the body is longer than that of testosterone (T). A study of transdermal 5α-DHT and testosterone treatment reported terminal half-lives of 2.83 hours and 1.29 hours, respectively. This half-life data for the transdermal 5α-DHT and testosterone has to be considered an estimate and it is clear that the process of transdermal drug delivery of 5α-DHT and testosterone via the epidermis, and dermis, and the skin appendages into the subcutis levels and then into a host of vascular areas has issues with regard to the washout of transdermally delivered 5α-DHT and testosterone.

Unlike other androgens such as testosterone, 5α-DHT cannot be converted by the enzyme aromatase into an estrogen like estradiol. Therefore, it is frequently used in research settings to distinguish between the effects of testosterone caused by binding to the AR and those caused by testosterone's conversion to estradiol and subsequent binding to and activation of ERs. Although 5α-DHT cannot be aromatized, it is still transformed into metabolites with significant ER affinity and activity. These are 3α-androstanediol and 3β-androstanediol, which are predominant agonists of the ERβ.

Applicant wishes to make clear that the common use of "DHT" as seen in the general literature, refers to 5α-DHT.

The applicant notes that while a great deal of chemistry, pharmacology, pharmacokinetics, and clinical pharmacology is known and in the literature for 5α-DHT, there is very little data published or available for healthy human beings, healthy mammals and animals on seemingly basic chemistry, pharmacology, pharmacokinetics, normal ranges of 5β-DHT in humans during embryogenesis, during infancy, during childhood, during puberty, during adolescence, during young adulthood, middle age adult years, the older age groups of over 50, over 60, over 70, over 80 y.o. in men and women, mammals or animals in healthy human males and females, mammals or animals.

Swerdloff et al., (Swerdloff R S, Dudley R E, Page S T, Wang C, Salameh W A. Dihydrotestosterone: Biochemistry, Physiology, and Clinical Implications of Elevated Blood Levels. Endocr Rev. 2017 Jun. 1; 38(3):220-254. doi: 10.1210/er.2016-1067. PMID: 28472278; PMCID: PMC6459338) identifies that common approach and convention used by the medical and scientific community is to refer to 5 Alpha Dihydrotestosterone (5α-DHT) as just "DHT". Thus, common use and convention by physicians, scientists and even the general public that the reference to "DHT" refers to 5 Alpha Dihydrotestosterone (5α-DHT).

As such, the disclosure draws clear distinction between DHT, whether termed "5 Alpha Dihydrotestosterone" (5α-DHT) or the 5 Beta Reduced metabolite of testosterone (T) that is precisely described as "5 Beta Dihydrotestosterone" (5β-DHT).

Benign Prostatic Hyperplasia (BPH)

A man's prostate gland continues growing throughout his life. That's why older men are more likely to have issues with enlarged prostate. This condition is at times referred to or called benign enlarged prostate by some authors and in lay papers, which isn't the same thing as having prostate cancer. These are two separate health conditions that are treated in different ways. Benign means noncancerous. However, even without cancer, an enlarged prostate can cause discomfort and complications.

Benign enlarged prostate is the most common problem for men over age 50. Men with this condition experience bladder troubles that include: frequent urination, involuntary loss of urine, a weak stream of urine, and pain during urination or after ejaculation.

It is of note that while there are pharmaceutical therapies that act as 5a Reductase enzyme inhibitors, such as finasteride, sold under the brand names, Proscar® and Propecia®, which may be used in certain embodiment of the disclosure, or avoided in certain embodiments described herein.

Low dose finasteride may result in side effects of fatigue, and even mental sluggishness. As such, finasteride may be an unacceptable pharmaceutical therapy for the prevention of scalp androgenetic alopecia. It is noted that while the discovery of 5α Reductase enzyme inhibitors was a major breakthrough in medicine, endocrinology, pharmacology, clinical pharmacology and science, it is known that there are many men who are not able to take these medications without deleterious side effects. In addition, there are well described human illness disorders for some men who have taken 5α Reductase enzyme inhibitors. This is not unexpected as many prescription medications, will have side effects and the potential for post use of the medication effects that can be bothersome of that will cause feelings of illness, sickness or poor health.

Disclosed herein is a novel, nonobvious and useful method of use of 5β-DHT as more fully described above, and below. It is clear that new, novel therapies are needed to prevent prostate disease, prostate cancer, and also prevent and or treat a wide range of health disorders as disclosed above and below. There are far too many human males, mammals and even animals that seem to have to wait for the natural history of aging and issues relating to aging, genetics & epigenetics or hormone action (particularly T and 5α-DHT) as these relate to prostate disorders (e.g. BPH) and prostate cancers. The same is true for scalp alopecia in human males and females.

With regard to BPH and impaired urine outflow from the bladder in human males, and dogs, and other animals it is the medical care custom or standard of care of many physicians to suggest to male patients that if symptoms aren't severe, a physician may recommend regular checkups for a period before deciding on medical treatment or surgical or interventional radiology treatments. The main form of medical treatment involves prescription drugs from these two categories: alpha blocker medications and 5-alpha reductase inhibitor medications. Alpha blockers reduce symptoms by relaxing the muscles in the prostate and bladder and 5-alpha reductase inhibitors work by blocking the formation of 5 Alpha Dihydrotestosterone hormone (a 5 alpha reduced metabolite testosterone) that has been clearly identified as a very important hormone that may cause the prostate to enlarge over in humans, mammals and animals.

The prostate gland is located beneath (distal) to the urinary bladder. In human males, mammals, and animals, and the tube like anatomic structure (the urethra) that transports urine from the urinary bladder, through the prostate gland, through the penis and ultimately empties urine out of the meatus of the penis passes through the center of the prostate gland in human males, mammals and animals. When the prostate enlarges, it begins to have a mass effect that can lead to the blockage of urine flow out of the bladder and this can lead to serious health issues for the bladder, for the kidneys and for overall health of a human male. Most human males have continued prostate growth throughout their life. In many men, (and male dogs) this continued growth enlarges the prostate enough to cause urinary outflow symptoms that may impair and significantly block urine flow out of the urinary bladder. As of Jun. 22, 2021, it is not entirely clear what causes the prostate to enlarge and the genetics, epigenetics and complex aspects of endocrine and intracrine molecular biology and cellular biology remain unknown by even the most leading edge experts in the fields of urology, endocrinology, genetics, epigenetics, and all areas of related science and medical research. However, it likely due to complex genetics, epigenetics and a host of endocrine and intracrine changes in the metabolism, interconversion of hormones, variations in hormone receptors, variations in hormone response elements (HRE) located on chromosomes, and a highly complex set of epigenetic and posttranscription events that relate to hormone actions and molecular biology and balance of sex hormones as men grow older.

Risk factors for prostate gland enlargement include:

Aging. Prostate gland enlargement rarely causes signs and symptoms in men younger than age 40. About one-third of men experience moderate to severe symptoms by age 60, and about half do so by age 80.

Family history. Having a blood relative, such as a father or a brother, with prostate problems means you're more likely to have problems.

Diabetes and heart disease. Studies show that diabetes, as well as heart disease and use of beta blockers, might increase the risk of BPH.

Lifestyle. Obesity increases the risk of BPH, while exercise can lower your risk.

Benign prostatic hyperplasia (BPH)—also called by some: prostate gland enlargement—is a common condition as men get older. An enlarged prostate gland can cause uncomfortable urinary symptoms, such as blocking the flow of urine out of the bladder. It can also cause bladder, urinary tract or kidney problems.

The severity of symptoms in people who have prostate gland enlargement varies, but symptoms tend to gradually worsen over time. Common signs and symptoms of BPH include:

Frequent or urgent need to urinate
Increased frequency of urination at night (nocturia)
Difficulty starting urination
Weak urine stream or a stream that stops and starts
Dribbling at the end of urination
Inability to completely empty the bladder
Less common signs and symptoms include:
Urinary tract infection
Inability to urinate
Blood in the urine.

The size of the prostate in humans, mammals and animals does not necessarily determine the severity of your symptoms. Some men with only slightly enlarged prostates can have significant symptoms, while other men with very enlarged prostates can have only minor urinary symptoms. In some men, symptoms eventually stabilize and might even improve over time.

Conditions that can lead to symptoms similar to those caused by enlarged prostate include:

Urinary tract infection
Inflammation of the prostate (prostatitis)
Narrowing of the urethra (urethral stricture)
Scarring in the bladder neck as a result of previous surgery
Bladder or kidney stones
Problems with nerves that control the bladder
Cancer of the prostate or bladder.

It is well established in the medical and scientific literature that the problems of prostate growth and prostate enlargement that commonly occurs after human males reach the age of 50 years old or 60 years old is a major public health problem and requires many medical, surgical, pharmaceutical, radiation therapy, radionucleotide targeted immune genetic therapies, chemotherapy health related interventions by physicians and health care systems. There are a host of medical, interventional, and surgical therapies used to treat disorders of the prostate gland in human males.

Thus there exist unmet needs for preventing issues with the prostate in humans, dogs, and other animals. While there are a number of therapies that are utilized by individuals, patients and physicians to seek to prevent or treat disorders of the prostate in humans, mammals and animals, there is a critical need for new, novel, nonobvious and useful therapeutic approaches and treatments to prevent, treat and managed issues that relate to disorders of the prostate: including prostate enlargement with reductions of urinary flow to empty the urinary bladder.

There are many human males who are hopeful, if not desperate, to seek so-called "natural" prophylactic therapies and even "natural" treatments for BPH and even to prevent prostate cancers. Some human males take saw palmetto formulations to seek to prevent or treat BPH and some take it to lower their risk of prostate cancer.

One 2016 review of clinical studies with a standardized extract of saw palmetto (called Permixon) found that the extract was safe and may be effective for relieving BPH-induced urinary symptoms compared against a placebo.

The generic name of saw palmetto, *Serenoa repens*, honors American botanist Sereno Watson. It is of interest that *Serenoa repens*, commonly known as saw palmetto, is the sole species currently classified in the genus *Serenoa*. It is a small palm, growing to a maximum height around 7-10 ft (2.1-3.0 m). It is endemic to the subtropical Southeastern United States, most commonly along the south Atlantic and Gulf Coastal plains and sand hills. It grows in clumps or dense thickets in sandy coastal areas, and as undergrowth in pine woods or hardwood hammocks.

As disclosed herein, the use of 5 Beta DHT may prove to be highly valuable with regard to the prevention and treatment of a number of prostate diseases and disorders, including BPH and prostate cancer. This may be a result of many factors, both endocrine and intracrine. It may also result in most novel interaction of 5 Beta DHT with the brain and pituitary gland and it may be that 5 Beta DHT formulations may reduce the production and levels of gonadotropin hormones and substances from the brain and CNS and in doing so reduce the levels of circulation Testosterone and also 5 Alpha Dihydrotestosterone. It may further lead to decreased levels of 5 Alpha DHT in the prostate gland and other issues, breast, ovary, and uterus and testicles) and in this way reduce the 5 Alpha DHT effects as promotors of cellular and genetic actions that are suggested as part of the "causative pathophysiology" of BPH in men, of prostate cancer, and also breast, ovarian, testicular and uterine cancer in human. This is a potential huge and heretofore neglected potential innovation in pharmaceutical therapeutics.

Breast Cancer

Glaser's paper describe 5α-DHT and testosterone in breast cancer prevention (R. Glaser, et al., Maturitas 82 (2015) 290-294.). They note both the abundance of testosterone and 5α-DHT in women, and the negative effects that imbalances in either or both hormones can cause including mental and physical health, immune function, glycemic control and inflammation any of which can impact cancer occurrence.

Prostate Cancer

Prostate cancer is cancer of the prostate gland in humans, mammals and animals. The prostate is a gland in the male reproductive system that surrounds the urethra just below (distal) the bladder. Some experts in urology, medicine, endocrinology, intracrinology, molecular biology and oncology suggest the if one were assess a large number of men at age 70 y.o. that one might find on autopsy or with prostate biopsy that perhaps over 50% of men aged 70 may show prostate cancer pathology.

Of note, prostate cancer can occur in young adult and middle aged human males and can lead to death in men who are in their 40's and 50's. This is just a horrible problem and shows how prostate cancer is not just a disease of men over 65 y.o.

There are few safe and effective pharmaceutical therapies, approved by the U.S. FDA for the use of pharmaceutical medications or therapeutics for the prevention of prostate cancer. While there are some scientists who believe that medications like 5 alpha reductase inhibitor medications may have a role in reducing the risk of prostate cancer, it is as of yet not a clearly established as a highly effective and also a well-tolerated form of pharmaceutical therapy to prevent prostate cancer or prostate disease in all men.

Most prostate cancers are slow growing. Cancerous cells may spread to other areas of the body, particularly the bones and lymph nodes. Prostate cancers may initially cause no symptoms. In later stages, symptoms include pain or difficulty urinating, blood in the urine, or pain in the pelvis or back. Benign prostatic hyperplasia may produce similar symptoms. Other late symptoms include fatigue, due to low levels of red blood cells. Factors that increase the risk of prostate cancer include older age, family history and race. About 99% of cases occur after age 50. A first-degree relative with the disease increases the risk two- to three-fold. Other factors include a diet high in processed meat and red meat, association with gonorrhea, and increased risk is associated with the BRCA mutations.

The state of the art for the prevention of prostate cancer or even BPH is clearly less than satisfactory for human, dogs, other mammals and animals. For human males, it is an accepted part of medical and urologic reality to most physicians and even many lay persons that human males are almost doomed to have BPH problems as well as prostate cancer as they get past the age of 50 y.o. or 60 y.o. or older. There is clearly a need for new, novel, nonobvious and useful inventions that include pharmaceutical therapies that are well tolerated, that have minimal side effects and that will decrease the number of human males, dogs, other mammals and animals that may develop prostate cancer or BPH.

Prostate cancer screening, including prostate-specific antigen (PSA) testing, increases cancer detection but whether it improves outcomes is controversial. Informed decision making is recommended for those 55 to 69 years old. Testing, if carried out, is more appropriate for those with a longer life expectancy. Although 5α-reductase inhibitors appear to decrease low-grade cancer risk, they do not affect high-grade cancer risk, and are not recommended for prevention of all forms of prostate cancer.

Many cases of prostate cancer are managed with active surveillance or watchful waiting. Other treatments may include a combination of surgery, radiation therapy, hormone therapy, or chemotherapy. Cancerous tumors of the prostate limited to the prostate may be curable. Pain medications, bisphosphonates, and targeted therapy, among others, may be useful. Outcomes depend on age, health status and how aggressive and extensive the cancer is. Most men with prostate cancer do not die from it; for example in the United States, five-year survival rate is 98%.

Rawla P, provides a comprehensive review of prostate cancer and associated statistics (Rawla P., Epidemiology of Prostate Cancer. World J Oncol. 2019 April; 10(2):63-89. doi: 10.14740/wjon1191. Epub 2019 Apr. 20. PMID: 31068988; PMCID: PMC6497009). In particular, the author notes that the occurrence and incidence of the diagnosis continues to increase and underscores to pressing need for additional and alternative therapies to those currently available.

The American Cancer Society's position regarding early detection by PSA testing is stated as lacking proof that "the potential benefits of testing outweigh the harms of testing and treatment. The American Cancer Society believes that men should not be tested without learning about what we know and don't know about the risks and possible benefits of testing and treatment" and generally suggests individual conversations with personal care physicians about testing should begin around age 50.

A number of tests can be used to gather information about the prostate and the urinary tract, which have been reviewed and are generally known in the art. In particular MRI and ultrasound may prove to be a valuable imaging and diagnostic method for assessing status of prostate health.

Androgen Hormones

Androgens (such as testosterone) are natural hormones made endogenously in humans, mammals and animals. They are important in sexual development in both men and women and are important for health and wellness.

In women, androgens are produced in small amounts by the ovaries and the adrenal glands. Higher levels of androgens in the blood may be linked to an increased risk of breast cancer in women.

Of the androgens, testosterone has been the most studied in relation to breast cancer risk.

Breast Cancer Risk after Menopause

Studies show higher blood levels of testosterone may increase the risk of breast cancer in postmenopausal women. There are a number of hormone related health disorders in woman (human females) of all ages and these include breast cancer, ovarian cancer, uterine cancer, thyroid cancer, and other cancers. There are a host of yet to be fully understood endocrine factors, including genetics and epigenetics of hormone actions, relating to androgen hormones, estrogen hormones, progesterone hormones and there metabolites that are felt to play a significant role in human females.

Erectile Dysfunction (ED)

Erectile dysfunction (ED) or impotence is described as continuous incapacity to attain and preserve a sufficient erection for a reasonably pleasurable sexual intercourse, and is associated with many etiologies (e.g., eurologic, psychologic, endocrinologic, or vascular). In about 80% of cases of ED, physical causes can be identified. These include cardiovascular disease; vascular disorders, veno-occlusive dysfunction of the penile veins, diabetes mellitus; neurological problems, such as those following prostatectomy; hypogonadism; and drug side effects. About 10% of cases are psychological impotence, caused by thoughts or feelings; here, there is a strong response to placebo treatment.

A variety of causes of or contributors to ED are known and include, for example, prescription drugs (e.g., SSRIs, beta blockers, alpha-2 adrenergic receptor agonists, thiazides, hormone modulators, and 5α-reductase inhibitors, neurogenic disorders (e.g., diabetic neuropathy, temporal lobe epilepsy, multiple sclerosis, Parkinson's disease, multiple system atrophy), cavernosal disorders of the penis (e.g., Peyronie's disease), hyperprolactinemia (e.g., due to a prolactinoma), psychological causes (anxiety, stress, and mental disorders), surgery (e.g., radical prostatectomy), aging, kidney failure, and lifestyle habits (e.g., smoking).

Injection Therapies For ED

Injectable alprostadil (synthetic prostaglandin E1) is prescribed for some men with ED and at times with increased doses. Some men are treated with three injectable medications including injectable Trimix (containing alprostadil, papaverine, and phentolamine).

In accordance with some embodiments of the disclosure, methods comprising 5 Beta DHT, used alone or in combination with other medications and hormones or therapies may be a safe and effective oral and/or injectable therapy for ED.

Surgical intervention for a number of conditions may remove anatomical structures necessary to erection, damage nerves, or impair blood supply. ED is a common complication of treatments for prostate cancer, including prostatectomy and destruction of the prostate by external beam radiation, although the prostate gland itself is not necessary to achieve an erection. As far as inguinal hernia surgery is concerned, in most cases, and in the absence of postoperative complications, the operative repair can lead to a recovery of the sexual life of people with preoperative sexual dysfunction, while, in most cases, it does not affect people with a preoperative normal sexual life.

Treatment depends on the underlying cause. In general, exercise, particularly of the aerobic type, is effective for preventing ED during midlife. Counseling can be used if the underlying cause is psychological, including how to lower stress or anxiety related to sex. Medications by mouth and vacuum erection devices are first-line treatments followed by injections of drugs into the penis, as well as penile implants. Vascular reconstructive surgeries are beneficial in certain groups. Treatments, other than surgery, do not fix the underlying physiological problem, but are used as needed before sex.

Medications

The PDE5 inhibitors sildenafil (Viagra), vardenafil (Levitra) and tadalafil (Cialis) are prescription drugs which are taken by mouth. As of 2018, sildenafil is available in the UK without a prescription. Additionally, a cream combining alprostadil with the permeation enhancer DDAIP has been approved in Canada as a first line treatment for ED. Penile injections, on the other hand, can involve one of the following medications: papaverine, phentolamine, and prostaglandin E1, also known as alprostadil. In addition to injections, there is an alprostadil suppository that can be inserted into the urethra. Once inserted, an erection can begin within 10 minutes and last up to an hour. Medications to treat ED may cause a side effect called priapism.

Prevalence of medical diagnosis of ED. In a study published in 2016, based on US health insurance claims data, out of 19,833,939 US males aged ≥18 years, only 1,108,842 (5.6%), were medically diagnosed with erectile dysfunction or on a PDE5I prescription (μ age 55.2 years, σ 11.2 years). Prevalence of diagnosis or prescription was the highest for age group 60-69 at 11.5%, lowest for age group 18-29 at 0.4%, and 2.1% for 30-39, 5.7% for 40-49, 10% for 50-59, 11% for 70-79, 4.6% for 80-89, 0.9% for ≥90, respectively.

Testosterone and ED

Men with low levels of testosterone can experience ED. Taking testosterone may help maintain an erection. Men with type 2 diabetes are twice as likely to have lower levels of testosterone, and are three times more likely to experience ED than non-diabetic men.

In accordance with some aspects and embodiments, the disclosure comprises therapeutic use of 5β-DHT used alone, or in combination with testosterone, 5α-DHT, vasodilator medications, and other currently used treatments, for helping men with ED. The methods may comprise any one or more known therapies for ED that are available and familiar to those of skill in the art, and/or as further described herein.

Prostaglandins for ED Treatment

Erection can be induced by injecting 10-20 μg of prostaglandin E1, with evaluations of the arterial flow every five minutes for 25-30 min (see image). The use of prostaglandin E1 is contraindicated in patients with predisposition to priapism (e.g., those with sickle cell anemia), anatomical deformity of the penis, or penile implants. Phentolamine (2 mg) is often added. Visual and tactile stimulation produces better results. Some authors recommend the use of sildenafil by mouth to replace the injectable drugs in cases of contraindications, although the efficacy of such medication is controversial.

Before the injection of the chosen drug, the flow pattern is monophasic, with low systolic velocities and an absence of diastolic flow. After injection, systolic and diastolic peak velocities should increase, decreasing progressively with vein occlusion and becoming negative when the penis becomes rigid (see image below). The reference values vary across studies, ranging from >25 cm/s to >35 cm/s. Values above 35 cm/s indicate the absence of arterial disease, values below 25 cm/s indicate arterial insufficiency, and values of 25-35 cm/s are indeterminate because they are less specific (see image below). The data obtained should be correlated with the degree of erection observed. If the peak systolic velocities are normal, the final diastolic velocities should be evaluated, those above 5 cm/s being associated with venogenic ED.

The term erectile dysfunction is not used for other disorders of erection, such as priapism.

Treatment involves addressing the underlying causes, lifestyle modifications, and addressing psychosocial problems. In many cases, treatment is attempted by drugs, specifically PDE5 inhibitors (such as sildenafil), which dilate blood vessels, allowing more blood to flow through the spongy tissue of the penis (akin to opening a valve further in order to allow more water to enter a fire hose). Other treatments, less commonly used, include prostaglandin pellets, inserted in the urethra; smooth-muscle relaxants and vasodilators, injected into the penis; penile implants; penis pumps; and vascular reconstructive surgery.

Hormone Sensitive Cancers

A hormone-sensitive cancer, or hormone-dependent cancer, is a type of cancer that is dependent on a hormone for growth and/or survival. Examples include breast cancer, which is dependent on estrogens like estradiol, and prostate cancer, which is dependent on androgens like testosterone and 5α-DHT. Hormones play important roles in our body, they're also effective in some types of cancer by promoting some tumors grow and spread, which are so-called hormone-sensitive or hormone-dependent cancer. A hormone-sensitive cancer, or hormone-dependent cancer, is a type of cancer that is dependent on a hormone for growth and/or survival. If a tumor is hormone-sensitive, it means that there are special proteins called receptors on cells surface. When the hormone bind the matched receptor, it results in growth and spread of cancer cells While tumor initiating event for hormone-related cancers can be varied, the promotion event and subsequent proliferation is driven by a sex hormone. Both endogenous and exogenous hormones, by driving cell proliferation, increased the number of cell divisions and the opportunity for random genetic errors to lead to cancer.

Big Four Hormone Related Cancers

The main types of Hormone-sensitive cancers are the following.

(1) Breast Cancer

Breast cancer is often hormone responsive, since growth or regression of tumors can often be regulated by appropriate endocrine manipulations. Estrogen and progesterone seem to be main hormones involved in growth of breast cancer.

(2) Ovarian Cancer

Ovarian cancer can be affected by estrogen. β-estradiol (E2) can stimulate the growth of some estrogen receptor (ER)-positive ovarian carcinoma cells, and these effects may be related with changes in the cellular levels of steroid hormone receptors.

(3) Uterine Cancer

Uterine or endometrial cancer are activated by estrogen and progesterone are related to this type. The uterine endometrium is extraordinary sensitive to steroid hormones, observation that women who ovulate and produce progesterone have an extremely low possibility to get endometrial cancer proves progesterone as a critical inhibitor of carcinogenesis.

(4) Prostate Cancer

Prostate cancer is dependent on androgens like testosterone and similar hormones that can help it grow and spread.

Treatments for hormone-sensitive-cancers include blocking the synthesis or action of the hormone or surgery to remove the organ that produces the hormone. Androgen deprivation therapy includes treatment with androgen receptor antagonists and/or surgical removal of the testes while estrogen deprivation therapy involves treatment with estrogen receptor antagonists and/or surgical removal of the ovaries.

Hormone Receptor Antagonists

Antiandrogens or antiestrogen are used to block the binding of androgen and estrogen to their respective nuclear hormone receptors and thereby blocks the proliferative effects of these hormone on hormone dependent cancer. For example, the antiestrogen tamoxifen used for the treatment of breast cancer while the antiandrogen bicalutamide alone or in combination with castration is used to treat prostate cancer. Interruption of hormonal stimulus. For example, tamoxifen can slow the progression until actual hormone independence occurs in the pathway later. In more recent years, evidence in support of this cell proliferation model of hormone responsive cancer etiology has continued to accumulate. Anti-hormone therapies are proved to be effective in stopping progression and thereby increasing the time to recurrence or death.

Receptor Agonists

Progesterone is regarded as the major endometrial tumor suppressor.

Hormone synthesis inhibitors are known for treatment to hormone dependent cancers. Various agents that block key events in the synthesis of hormones are sometimes used to treat hormone dependent cancers. Aromatase inhibitors such as anastrozole block the synthesis of estrogen while CYP17A1 inhibitors such as abiraterone block the synthesis of androgen.

Gonadotropin-releasing hormone antagonists blocks the signaling that stimulates androgen synthesis.

Surgery for hormone dependent cancers:
As the growth of hormone dependent cancer is driven by sex hormones, surgical removal of the organs that synthesizes the sex hormone is sometimes performed. In the case of prostate cancer, orchiectomy (surgical castration) of the testes is sometimes performed while oophorectomy (surgical removal of the ovaries) is sometimes performed to prevent breast cancer in high risk women with BRCA1 or BRCA2 mutations Hirsutism In Women 5 Beta DHT may be a safe and effective therapy for the prevention and treatment of hirsutism. There are disorders of human women that relate to excess hair growth such as hirsutism. Disorders described as hirsutism are very serious disorders to assess, diagnose properly, and also treat with properly tailored therapies. There is a key role of endocrine issues and abnormalities in many women with hirsutism.

There are serious disorders in women relating to androgenetic alopecia (sometimes referred to as male pattern baldness) and also a pattern of scalp alopecia referred to as female pattern baldness. There is a frontal scalp fibrosing alopecia noted in women and some men that relates to a number of endocrine issues and also to past use of hormone therapies for a variety of medically indicated uses. This includes use of estrogens, birth control pills by women and other uses of hormones and medications.

Generally, a "disease" is to be defined as any disorder of health that a physician, scientist, veterinarian of ordinary skill in the art would consider to be a health disorder, an illness, a deviation from well recognized definitions of health status, or disorders or problems that people, mammals or animals may have that may relate to disorders of aesthetics that may include hair growth disorders, hair loss disorders, cosmetic dermatology disorders, and disorders that cause what might be called health related concerns. The definition of health as outlined by the World Health Organization (WHO) Constitution in the post WW II period (and as currently put forth on its Internet website page of Jun. 22, 2021) is a view of what the applicant considers global health hopes—and perhaps better said global public health—in a world that is not one with starvations, pestilence, poverty, hunger, a lack of access to medical care and medications— and perhaps also a world of global human health and geopolitical health as it relates to the most impoverished, war torn or horrible climate change conditions that is (and are) aspirational goals for global health and wellness for the end of hunger, rampant illness, starvation, human misery of untold proportions and poverty and war related atrocities of the human condition. While the WHO discussions of health is of some value, as it relates to goals for better health to human populations around the world, in many ways, it is not used by practicing physicians, health care professionals, veterinarians and health care professions to assess the presence of health disorders, diseases, injuries, age related issues that are common over the life span of human beings, mammals and animals. Beyond the concept of well recognized diseases, health disorders, disease states, traumatic health issues, mental health issues and traditional disorders described in leading textbooks in internal medicine, endocrinology, pediatrics, neurology, psychiatry, emergency medicine, dermatology, pharmacology and clinical pharmacology, there are problems and concerns human beings have with regard to their appearances, their aesthetics and aesthetic medicine that are well understood by physicians, health care experts, veterinarians and scientists. While the WHO definition of health goes beyond the absence of disease, it is also well recognized by physicians, nurses and health care professionals and scientists that the WHO definition of health is not the definition used by clinicians, physicians, veterinarians, and health care professionals who treat human beings, mammals or animals with diseases, health disorders, deviations from normal health definitions of health, and may include aesthetic disorders or disorders of sexual dysfunction (e.g., erectile disease, libido, etc.), disorders of alopecia of the scalp or other parts of the body of a human, mammal or animal.

In an aspect, the disclosure relates to use of 5 Beta DHT in the treatment and prevention of prostate health disorders and/or disease, including recognized prostate disease states (such as BPH, BPH urinary retention, and prostate cancers).

While some authors of medical and scientific papers as well as endocrinology and urology papers have suggested the 5 Alpha Dihydrotestosterone (5α-DHT) might have beneficial effects and/or protective effects on the human prostate when used as a pharmaceutical therapy to increase blood levels and serum levels of 5 Alpha DHT. One theory is that by increasing the levels of total blood and serum levels of 5 Alpha DHT that this acts on the brain to decease the secretion of pituitary gonadotropin hormones (LH, FSH etc. . . . ) and that this leads to a decrease of production of testosterone (T) and also lower levels of blood and serum testosterone. This decrease in blood and serum total testosterone has the physiological effect of less circulating total testosterone and lower blood and serum levels of free testosterone. This lowers blood and serum testosterone levels of as they relate to the potential lower level of circulating serum T in the blood that reaches the prostate circulation and prostate cells, and other androgen sensitive glands or tissues in humans, mammals and animals as it relates to cancers with a known relationship to androgen and other sex steroid hormones.

In an aspect the disclosure relates to the use of 5β-DHT, as described in this document, for treatment and/or prevention of BPH in the prostate, treat BPH in the prostate, prevent prostate cancer, treat prostate cancer, or treating and preventing cancers including but not limited to breast cancer, uterine cancer, ovarian cancer, testicular cancer and other cancers.

In an aspect the disclosure relates to 5 Beta DHT and its use in a variety of formulations and drug delivery pathways, that may prevent or reduce scalp alopecia disorders.

In an aspect, the disclosure relates to 5 Beta DHT used in a variety of formulations and drug delivery pathways, that may be useful pharmaceutical therapy for the prevention and treatment of cardiovascular disease, central nervous system disease, endocrine disorders, cancers of many types.

The molecular formula of 5β-DHT is:
Molecular Formula $C_{19}H_{30}O_2$
The molecular weight of 5β-DHT is 290.4 g/mol.
5 Beta Dihydrotestosterone may be referred to herein as 5β-DHT, 5 Beta DHT, or 5beta-dihydrotestosterone.
5 beta-dihydrotestosterone (5β-DHT) is a 17beta-hydroxyandrostan-3-one that has beta-configuration at position 5. It is a metabolite of testosterone. 5β-DHT has a role as an androgen, a mouse metabolite, a vasodilator agent and a human metabolite. It is a 17beta-hydroxyandrostan-3-one and a 3-oxo-5beta-steroid.

Androgenetic Alopecia (AGA)—in Men

Androgenetic alopecia (AGA) is the most common cause of hair loss in both men and women. In men, the condition is characterized by hair loss in a well-defined pattern causing recession of the hair line in a typical M-shaped pattern, along with thinning of the hair vertex, resulting in progression to partial or complete baldness in the majority human male cases. In women, scalp hair loss can affect the mid-frontal area without recession of the hair line and rarely progresses to complete baldness (Sinclair, 1998).

Several factors, including genetic and environmental agents, play a pivotal role in the pathogenesis of AGA. The hair growth cycle starts with anagen, in which a follicle begins growing new hair, and is regulated by several cytokines (Su et al., 2017). An increased level of androgen in the hair follicles leads to a shorter cycle of hair growth and shorter and thinner hairs (miniaturization; Ellis et al., 2002). Other mediators, including the insulin-like growth factor (IGF) family, may affect the hair follicle cycle. IGF-1 has been shown to promote hair follicle growth and prevent entrance into a catagen-like state.

Female Pattern Scalp Alopecias

Female pattern AGA is considered a common hair disorder that starts in the third decade of life, reaching its peak after the age of 50 years. AGA may affect up to 40% of women at some point in their life, with significant effects on quality of life (Ahluwalia and Fabi, 2019). Different medications, such as minoxidil (2% or 5%), flutamide, dutasteride, finasteride, and spironolactone, as well as cosmetic hair procedures, including hair transplantation, are the existing treatment options for AGA. However, improvement and hair regrowth cannot always be achieved with the usual remedies. Thus, an increasing interest exists for finding new medications that affect the hair growth cycle.

Anagen is the active growth phase of hair follicles during which the hair matrix can divide rapidly, adding to the hair shaft. The length and thickness of each hair shaft depend on the duration of the anagen phase. Miniaturization of the hair follicle, which is a characteristic feature of AGA, is partially due to progressive shortening of the anagen phase. Fibroblast growth factor-7 (FGF-7) plays a critical role in reentering the hair follicle into the next anagen phase. Placenta may affect hair growth by inducing FGF-7. However, the mechanism by which placenta enhances proliferation and promotes hair growth remains to be elucidated (Werner and Grose, 2003).

As disclosed herein, 5 Beta DHT may increase any number of hair growth factors (including, but not limited to, Fibroblast growth factor-7 (FGF-7) that may prolong the anagen phase of the hair growth cycle in terminal hair follicles and intermediate and vellus hair follicles located on the scalp of human males, female as well as in mammals and animals.

Foams

In an aspect, the disclosure relates to a topical foam of 5 Beta DHT as a safe and effective therapy, for wound healing, prevention of scalp alopecia and other hair biology disorders.

In embodiments, 5 Beta Dihydrotestosterone (5β-DHT) may be of particular benefit with regard to the promotion of hair follicle health and also the prevention and/or treatment of hair loss disorders that are commonly referred to as alopecia by physicians and scientist who study hair biology, normal hair growth patterns and hair growth cycles. 5β-DHT may be particularly beneficial and a pharmaceutical therapy used to prevent what is commonly referred to as "androgenetic alopecia" of the scalp. androgenetic alopecia" of the scalp is sometimes referred to as "male pattern baldness". It is important to note that androgenetic alopecia can and does occur in both human males and also human females.

In embodiments, 5β-DHT may be particularly beneficial and a pharmaceutical therapy used to prevent and/or treat what is commonly referred to as "female pattern baldness".

In embodiments, 5β-DHT may be particularly beneficial and a pharmaceutical therapy used to prevent and/or treat what is commonly referred to as "female pattern baldness".

There are a number of ways and physiologic mechanisms that the therapeutic use of 5β-DHT may help prevent scalp hair loss in both humans and mammals, and some of these relate to direct effects of 5β-DHT on the cell populations that comprise the hair follicle structures in the male and female human body, mammalian body or animal body. In addition, there may be a number of indirect efforts of the therapeutic use of 5β-DHT that relate to the changes in the level of circulating hormones, particularly androgen hormones that include but are not limited to testosterone (T) and 5 Alpha DHT.

In embodiments, 5 Beta Dihydrotestosterone (5β-DHT) may be of particular benefit with regard to having protective clinical pharmacology effects on the hormone levels in the human body that are thought to be related to the risk of prostate health, prostate disorders such as benign prostatic hyperplasia (BPH).

In embodiments, 5 Beta Dihydrotestosterone (5β-DHT) may be of particular benefit with regard to having preventative & protective cancer prevention clinical pharmacology effects that lower the risk of the development of prostate cancer in human male and mammals. on the hormone levels in the human body that are thought to be related to the risk of prostate health, prostate disorders such as benign prostatic hyperplasia (BPH).

In embodiments, 5 Beta Dihydrotestosterone (5β-DHT) may be of particular benefit with regard to having beneficial oncology protective clinical pharmacology effects that lower the risk of the development of breast cancer, ovarian cancer, prostate cancer and other cancers that can and do occur in human males and females, was well as in mammals. on the hormone levels in the human body that are thought to be related to the risk of prostate health, prostate disorders such as benign prostatic hyperplasia (BPH).

In embodiments, 5 Beta Dihydrotestosterone (5β-DHT) may be of particular benefit with regard to having beneficial physiological effects in the treatment of erectile dysfunction when uses alone or in combination with other pharmaceutical therapies.

In embodiments, 5 Beta Dihydrotestosterone (5β-DHT) may be of particular benefit with regard to promoting wound healing in human being and mammals. It is a potent vasodilator.

In embodiments, 5 Beta DHT may promote hair growth on the scalp of humans, mammals and animals.

In embodiments, the disclosure provides a composition and method comprising the topical application of 5 Beta Dihydrotestosterone (5 Beta DHT), used alone or in fixed combination with other hair growth medications; including other androgens, bimatoprost, prostamides, prostaglandins, minoxidil or apocrine hair growth factors to promote and enhance hair growth in humans or animals, utilizing liquids, lotions, ointments, creams, gels, foams, sprays or aerosols or other solvents.

At birth, the average healthy human is born with 5 million hair follicles on the body. Of these, 1 million hair follicles are located on the head, with 100 thousand hair follicles located on the scalp area. Of note, scalp hair follicles, as well as eyebrow and eyelash hair follicles are not dependent on androgen hormones to produce hair growth. After birth, no new hair follicles are created on the human skin.

All hair, both human and animal, passes through a life cycle that includes three phases, namely, (1) the anagen phase (2) the catagen phase and (3) the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one begins to grow.

Now, under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

The skin is a multifunctional and multicompartment organ affected by diseases and their treatments. The bulk of percutaneous absorption of most agents is through the *stratum corneum*, which covers the entire skin surface. Of note, hair follicles and hair shafts can also play an important role in absorbing topical medications and compounds applied to the surface of the skin. Epidermal structure and sweat glands are also potential pathways of absorption of topically applied medications or hair growth agents. Hair follicles form a lipid-rich pathway for drug absorption and also represent a special shunt pathway to allow for a direct pathway for topical medications to reach key hair follicle structures and also provides a localized drug reservoir that can enhance local effects of medicines in the hair follicles.

The absorption of drugs and chemicals into and onto hair shafts also can be used to measure prior drug exposure.

Compositions and methods comprising 5 Beta dihydrotestosterone in specific hair follicle cellular activity located in the scalp hair follicles is not known. It may be scalp hair follicle "Follicular Protective" by indirect systemic and localized (hair follicle) endocrine and/or intracrine actions that lower levels of testosterone and 5 Alpha DHT.

Some scientists suggest that there are basically two types of hair, soft lanugo hair called vellus hair, and a thicker, coarser hair called a terminal hair. Vellus hair is all over the body except for the palms and soles. Hair growth can be further differentiated as being either androgen dependent or androgen independent hair. This distinction becomes important during puberty and throughout adulthood. Other scientists have noted an intermediate type of hair that is on the continuum between vellus hair and terminal hair.

Hair growth on the scalp is not solely dependent on androgen hormones. However, hair loss on the scalp leading to male or female pattern hair loss is often related to both genetics, epigenetics and the effects of testosterone (T) and 5 Alpha dihydrotestosterone (DHT) (as well as other complex genetic, epigenetic, and intracrine factors) that lead to the loss of active scalp hair follicles that can produce either vellus or terminal hairs.

Hair growth of eyelash hair or eyebrow hair is not androgen dependent. As with scalp hair, young children with normal health are usually able to grow scalp hair, eyelash hair and eyebrow hair before puberty.

In the epidermis, the *stratum corneum* is the outer layer and is 5-600 microns thick. The *stratum corneum* is the major barrier to percutaneous absorption of drugs and also helps minimize the loss of water from the body. It is made of "dead" epidermal cells that cannot reproduce and have lost their nuclei and mitochondria. It possesses multiple proteins and lipids that may reversibly or irreversibly bind drugs. Many chemicals and physical treatments to enhance percutaneous absorption work within the *stratum corneum*. Many drugs may partition into the *stratum corneum* and can function as a reservoir for drugs that will diffuse into the rest of the skin, even after topical application of the drug has ceased. The *stratum corneum* varies in thickness. Facial and post auricular have the thinnest *stratum corneum*.

The living layers of the epidermis with metabolically active cells comprise a layer of ~100 microns thick. The lowest or basal layer of the epidermis is called the *stratum basale* and is responsible for the bulk of cell division. Several cell layers in the spinous layer (*stratum spinosum*) contain cells that actively synthesize most epidermal proteins, especially keratins. The uppermost layer of the living epidermis is the *stratum granulosum*. This layer is where extracellular lipids are extruded from the epidermis.

There is a superficial capillary plexus of blood vessels between the dermis and epidermis that is the site of the majority of the systemic absorption of cutaneous drugs. There are a large number of lymphatics as well in this area.

The dermis is about 1,200 microns thick that is in part composed of collagen and proteoglycans that may bind drugs. Below the dermis, is a subcutaneous tissue called the hypodermis.

The hair shaft is formed by keratinized cells containing highly organized material. Hair has the appearance of an extremely elongated cylinder. The hair shaft has three (3) regions: The cuticle, the cortex and the medulla found close to the center of the hair shaft.

Lanugo hairs, the first body hairs formed in the embryo, are vellus in character, but often longer than the vellus shafts of the adult. The vellus hair shaft is short, thin, fine, lightly pigmented, and with no medulla. A vellus hair follicle is defined as a small follicle that extends no deeper than the upper dermis and produces a shaft no wider than its internal root sheath. Although vellus follicles may lack arrector pili muscles in some areas, vellus hair follicles are associated with these structures on the face. With maturity and exposure to androgens, regional human hair follicles switch in morphology to terminal follicles that produce terminal hair shafts. The inverse terminal-to-vellus switch occurs on the scalp of the genetically susceptible androgenic alopecia individuals after exposure to androgens.

The hair cycle appears to be central to the vellus-to-terminal hair follicle switch because phenomenologically the cycle appears to initiate that process; the follicle must cycle in order for the switch to occur. We do not yet know how the cycle is related to this transformation, although it may be due to a gradual change in the size of the papilla with the completion of each cycle. Relatively little attention has been given to this switch phenomenon mechanistically; in fact, even the follicle that characteristically switches has not yet been fully characterized.

The wide response range of hair to androgens reflects inherent genetic differences of hair depending on body site. There is a graded response of regional hairs to androgen levels; inguinal and axillary follicles, for example, are stimulated to grow under low levels of androgen, and facial hair to high levels, while deep temporal/occipital scalp and eyebrow/eyelash hair are insensitive to androgen levels altogether. This principle underlies the success of scalp hair transplants for male pattern balding, where androgen-insensitive hairs (occipital area) are transplanted to sites of androgen-sensitive hairs (frontal, parietal, coronal areas). Thus one must distinguish between hairs that are androgen dependent (axilla, mustache, beard and chest), androgen insensitive (eyebrow and eyelash), and androgen independent but androgen sensitive (scalp vertex in susceptible individuals). Ultimately, these interfollicular and interregional differences must stem from the way a given follicle is genetically programmed and how it responds to androgen stimulation, its androgen target genes, and the nature of its androgen receptor-mediated signal transduction events. Unfortunately, these parameters have not yet been dissected.

Hair growth during and after puberty of mature terminal hairs on the face in the mustache and beard areas is androgen dependent. The same is true for terminal hair growth in the chest and other parts of the male body. This process begins in puberty in boy who are developing secondary sex characteristics on their way to becoming young adult men.

Hair biology and hair loss physiology are complex and relate to a wide range of genetic variables, ethnic background, family history & genetics, health status, medication use, diet and even psychosocial stress levels.

The exploration and investigation of possible treatment options for treating scalp alopecia disorders in humans, mammals and animals and promotion hair growth in humans, mammals and animals requires an in depth understanding of hair biology, endocrinology, genetic hair growth variables in both sexes, and hormonal regulation of hair growth factors in different areas of the skin.

Genetics and epigenetics plays an important role both in the density and number of hair follicles in the mustache, beard and chest hair areas. In addition, genetics and epigenetics may determine the number of androgen receptors located in individual hair follicle cells on the scalp, face and chest. Further, genetics and epigenetics helps to determine the level and activity of the enzymes 5 alpha reductase 1, 2 and 3 that often play an important role within the body and also in the hair follicle cells relating to the growth of mature terminal facial hair, mustache hair, beard hair, chest hair and other androgen dependent hair growth.

Ethnic origin, and geo ethnic origin, and ancestry can play an important role and have a great impact on the hair growth in men. This is true for body hair, scalp hair, facial hair growth, chest hair growth, scalp hair growth and hair growth on the entire body.

All naturally occurring androgens play a critical role in human health and all androgens have major conversions and important metabolic pathways for interconversion into other hormones, other steroid hormones and other sex hormones. The same is true for animals.

It is well known that at the cellular level, testosterone is routinely converted into to 5 Alpha dihydrotestosterone via the enzymes five alpha reductase 1, 2 and 3. This conversion of testosterone to 5 Alpha dihydrotestosterone within hair follicles, that commonly happens within cells (to a variable degree), creates a very powerful anabolic androgenic steroid hormone, 5 Alpha dihydrotestosterone (5 Alpha DHT), that is 2 to 5 times more potent and powerful than testosterone in causing a wide range of physiologic effects in the body. This is particularly true with regard to androgen dependent hair growth in the human body compared to testosterone. The same is true in mammals and animals.

In a general sense, the disclosure provides the use of 5 Beta DHT as a compound, used alone or in combinations with other hormones, other medications and other pharmaceutical therapies, containing formulations, and discloses methods for many novel uses as disclosed herein, comprising the steps of administering systemic and/or topical pharmaceutically acceptable formulations of 5 Beta dihydrotestosterone, used alone or in fixed combination with other hair growth medications; including other androgens, 5 alpha reductase inhibitors, androgen receptor blocking agents, bimatoprost, prostamides, prostaglandins, minoxidil or apocrine hair growth factors.

In embodiments, the composition and method includes the use of 5 Beta dihydrotestosterone as a topical monotherapy for the promotion and enhancement of scalp hair growth. The topical composition of 5 Beta dihydrotestosterone may be of the 0.001% to 95%. The composition and method includes the topical application of such formulations to adolescents or adults.

In embodiments, the 5 Beta dihydrotestosterone (5β-DHT) topical formulations used in the method of the invention additionally comprises one or more additional other medications, for example additionally comprise one or more non-steroidal alopecia treatment agents, for example minoxidil, 0.001% to 10% w/v, or one or more hair growth promoters including prostamindes or prostaglandins, further including travoprost, latanoprost or bimatoprost 0.001% to 0.1% w/v and most preferably 0.03% w/v. These formulations can be administered as intravenous, injections, via drug delivery catheters, or using topical liquids, lotions, ointments, solutions, gels, foams, or sprays. The topical formulations are formulated so as to deliver the active ingredient(s) to the hair follicles and the bulb matrices of hair follicles, or to the mesenchymal dermal papilla cells of the hair follicles and also hair follicle structures that can be reservoirs for applied formulations.

In embodiments, 5β-DHT may be formulated so that the topical formulation can be absorbed into the hair follicle structures on the scalp or areas of the skin in humans, mammals or animals in a targeted manner. In addition, to allow the formulation to also adsorb onto a hair shaft itself and be drawn by capillary action to the target hair follicle bulb and other hair follicle structures. Additional useful formulation properties are the ability to cross the surface of the skin and travel to the hair follicle bulb matrix by trans-epidermal diffusion or by transdermal diffusion, following Fickes' laws of diffusion. This is beneficially accomplished by the addition of one or more dermal penetration enhancement agents, such as a lower alcohol, including methanol, ethanol, propanol, or isopropanol.

In embodiments, the topical formulations can be formulated to cause the active ingredient(s) to penetrate the layers of the epidermis and dermis sufficiently to reach the hair follicles and the hair follicle bulb matrices.

In embodiments, the concentrations of 5 Beta dihydrotestosterone may run in a range of from about 0.001% to about 50%, measured w/w, /w/v, or v/v. In some further embodiments, concentrations of 5 Beta dihydrotestosterone range from about 0.5% or about 1.0% to about 25%, measured w/w, w/v, or v/v.

In additional embodiments, the concentration of 5β-DHT may be from about 0.5% to about 25%; in further additional embodiments, the concentration of 5β-DHT may be from about 0.5% to about 10%; from about 0.5% to about 5%; or from about 0.5% to about 2%. Concentrations may be measured in weight to weight, weight to volume or volume to volume.

Additional topical formulation ingredients include pharmaceutically acceptable preservatives such as benzalkonium chloride, 0.2 to 0.5 mg/mL, sodium chloride, dibasic sodium phosphate, citric acid, and pharmaceutically acceptable purified water, eg. distilled water, reverse osmosis water, and so on. An aspect provides a topical formulation can contain 5 Beta dihydrotestosterone as a monotherapy or in any fixed dose combination with one or more of minoxidil, the prostamide bimatoprost, other prostamides and prostaglandin analogs, including travoprost, or latanoprost.

In embodiments, the composition and method of use 5 Beta Dihydrotestosterone (5β-DHT) (17β-hydroxy-5β-androstan-3-one) pharmaceutical formulations used alone, or in fixed combination, with other hormones, hormone analogues, medications, health supplements, and/or genomic and nanotechnology therapeutics, using multiple drug delivery routes of administration, for the promotion of health, the prevention of illness and disease, and treatment of human, mammalian and animal illness and disease and health conditions, health disorders and health related pathophysiology or physiologic disorders, including, but not limited to cardiovascular disorders, endocrine disorders, prostate disorders, breast disorders, vascular disorders, oncology and cancer disorders and diseases, central nervous system disorders including dementia and cerebrovascular diseases, dermatology disorders, scalp alopecia disorders, hair biology disorders, erectile dysfunction, Peyronie's disease, birth control therapy, and many types of cancer related to hormone action in humans, mammals and animals.

While the aspects disclosed herein may be embodied in many different forms, several specific embodiments are discussed herein with the understanding that the present disclosure is to be considered only as an exemplification of the principles of the invention, and it is not intended to limit the invention to the embodiments illustrated. Where the disclosure is illustrated herein with particular reference to 5 Beta dihydrotestosterone (5 Beta DHT), it will be understood to those skilled in the art that any metabolite of 5 Beta DHT can, if desired, be substituted in whole or in part for 5 Beta dihydrotestosterone in the methods herein described.

In one embodiment, the present invention is directed to a method for topical administration of 5 Beta dihydrotestosterone in a liquid, lotion of gel. The liquid, lotion of gel comprises 5 Beta dihydrotestosterone (5β-DHT), used alone or in combination with another androgen, that would be applied to the outer surface of skin areas where a person would hope to increase hair growth in the scalp areas. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

In another embodiment, the present invention is directed to a method for topical administration of 5 Beta dihydrotestosterone in a lotion. The lotion comprises 5 Beta dihydrotestosterone used alone or in fixed combination with other hair growth medications; including other androgens, bimatoprost, prostamides, prostaglandins, minoxidil or apocrine hair growth factors to promote and enhance hair growth of scalp hair growth in humans, mammals or animals that would be applied to the outer surface of skin areas where a person would hope to increase terminal and intermediate scalp hair growth. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

Other embodiments of this invention are directed to a method for topical administration of 5 Beta dihydrotestosterone in a foam, cream, a gel, an aerosolized spray, foam or other manner for delivering 5 Beta dihydrotestosterone, used alone or in fixed combination with other hair growth medications; including other androgens, bimatoprost, prostamides, prostaglandins, minoxidil or apocrine hair growth factors to promote and enhance hair growth of scalp hair growth in humans or animals that can be applied to the outer surface of skin areas where a person would hope to increase scalp hair growth. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

As used herein, the term "lower alcohol," alone or in combination, means a straight-chain or branched-chain alcohol moiety containing one to about six carbon atoms. In one embodiment, the lower alcohol contains one to about 4 carbon atoms, and in another embodiment the lower alcohol contains two to about 3 carbon atoms. Examples of such alcohol moieties include methanol, ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP, or in any common form including in combination with various amounts of water.

In one embodiment, the present invention is directed to a method for the topically application of 5β-DHT for percutaneous administration (transdermal use) of 5 Beta dihydrotestosterone applied the skin used alone or in combination, in a hydroalcoholic gel. The gel comprises one or more lower alcohols, such as ethanol or isopropanol; a penetration enhancing agent; a thickener; and water. In one embodiment, the gel comprises an anionic polymer thickening agent precursor neutralized with a hydroxide releasing agent, such as, e.g., sodium hydroxide. Additionally, the present invention may optionally include salts, emollients, stabilizers, antimicrobials, fragrances, and propellants.

In some embodiments, the derivative 5 beta dihydrotestosterone undecanoate may be used. 5 Beta dihydrotestosterone undecanoate for oral use may be provided as a gelatin capsule containing 5 beta dihydrotestosterone undecanoate, a fatty-acid ester of dihydrotestosterone. 5 beta dihydrotestosterone undecanoate is an androgen, is formed by cleavage of the ester side chain of 5 beta dihydrotestosterone.

In further embodiments, 5 alpha dihydrotestosterone undecanoate may also be used and may also be provided as a gelatin capsule containing 5 alpha dihydrotestosterone undecanoate, a fatty-acid ester of dihydrotestosterone. 5 alpha dihydrotestosterone undecanoate is also an androgen, is formed by cleavage of the ester side chain of 5 alpha dihydrotestosterone.

In additional embodiments, the 5 alpha dihydrotestosterone undecanoate can comprise a fixed combination with 5 beta dihydrotestosterone undecanoate for oral use as a gelatin capsule containing 5 alpha dihydrotestosterone undecanoate, a fatty-acid ester of dihydrotestosterone and 5 beta dihydrotestosterone undecanoate.

In embodiments, the concentrations of 5 Beta dihydrotestosterone undecanoate and/or 5 alpha dihydrotestosterone undecanoate may run in a range of from about 0.001% to about 50%, measured w/w, /w/v, or v/v. In some further embodiments, concentrations of 5 Beta dihydrotestosterone undecanoate and/or 5 alpha dihydrotestosterone undecanoate range from about 0.5% or about 1.0% to about 25%, measured w/w, w/v, or v/v.

In additional embodiments, the concentration of 5 Beta dihydrotestosterone undecanoate and/or 5 alpha dihydrotestosterone undecanoate may be from about 0.5% to about 25%; in further additional embodiments, the concentration of 5 Beta dihydrotestosterone undecanoate and/or 5 alpha dihydrotestosterone undecanoate may be from about 0.5% to about 10%; from about 0.5% to about 5%; or from about 0.5% to about 2%. Concentrations may be measured in weight to weight, weight to volume or volume to volume.

An alternative embodiment provides pharmaceutical fixed compositions for topical application to enhance hair growth comprising an effective amount 5β-dihydrotestosterone with cyclopentane N-ethyl heptanamide-5-cis-2-(3α-hydroxy-5-phenyl-1-trans-pentenyl)-3,5-dihydroxy, [$1_\alpha,2_\beta,3_\alpha,5_\alpha$], also known as bimatoprost, along with minoxidil.

Another aspect provides methods for decreasing the rate of scalp terminal hair follicle and hair loss of terminal hairs in human males, females, mammals and animals as well as stimulating the rate of scalp hair growth and for enhancing the conversion of vellus hair or intermediate hair to growth as terminal hair in a human or non-human by administering to the skin an effective amount of 5β-dihydrotestosterone, androgen receptor blocking agents, 5 alpha reductase inhibitors, bimatoprost and minoxidil, wherein the additional combination of bimatoprost and minoxidil obtains the above results in a synergistic manner as compared to bimatoprost and minoxidil, alone.

Another aspect provides methods for preventing prostate disorders and diseases in humans, dogs, mammals and animals.

Another aspect provides methods for preventing and treating disorders of erectile dysfunction when 5β-DHT is used alone or in combination with other medications used to promote and enhance vascular blood flow to the penis and to enhance penile erections.

The terms "effective amount", "therapeutically effective amount" or "pharmaceutically effective amount" as used herein refers to that amount of the therapeutic agent sufficient to ameliorate one or more aspects of the disorder. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

Embodiments may specifically include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "disease" or "health disorder" refers to any deviation from the normal health of a mammal and includes a state when disease symptoms are present, as well as conditions in which a deviation (e.g., infection, gene mutation, genetic defect, etc.) The applicant has made clear that the WHO definition of health is not a definition used by practicing physicians and health care providers to assess a well-recognized disease, illness, health condition or even a health condition that may be an aesthetic disorders such as scalp alopecia, dermatology related disorders or age and other aesthetic disorders that human beings consider to be a problem of health or a problem of aesthetics. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient, a mammal or an animal.

As used herein, "topical application," "topical administration," and "topically administering" are used interchangeably herein and include the administration of a composition to the skin, the scalp, upper and/or lower eyelid margin, eyebrow region, scalp or face. Topical application or administering may result in the delivery of an active agent to the eye or skin or a localized region of the body.

"Topical formulation" and "topical pharmaceutical composition" are used interchangeably herein and include a formulation that is suitable for topical application to the skin, penile surgery, the urethra via pellet formulations, the face, upper lip or chest areas. Specific topical formulations can be used for topical, local, regional, or transdermal application of substances.

The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." "About" may also include variations in the amount that a regulatory body such as the FDA or EMEA would view as bioequivalent to the claimed amount.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic acid, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

"Prodrugs" refer to compounds which are a precursor of a compound and that is converted into its active form, for example, in the body by normal metabolic processes.

Alopecia (baldness) a deficiency of either normal or abnormal hair is primarily a cosmetic problem in humans. It is a deficiency of terminal hair, the broad diameter, colored hair that is readily seen. However, in the so-called bald person although there is a noticeable absence of terminal hair, the bald scalp skin may contain vellus hair which is a fine colorless hair which may require microscopic examination to determine its presence. This vellus hair is a precursor to terminal hair. In some case of scalp alopecia, hair follicles have been destroyed by the long term impact of 5 alpha reductase and the impact of dihydrotestosterone, and other factors.

Drug synergism occurs when drugs can interact in ways that enhance, magnify or synergistically amplify one or more desired effects, or side effects, of those drugs. Negative effects of synergy are a form of contraindication such as when more than one depressant drug is used that affects the central nervous system (CNS), an example being alcohol and Valium. The combination can cause a greater reaction than simply the sum of the individual effects of each drug if they were used separately. In this particular case, the most serious consequence of drug synergy is exaggerated respiratory depression, which can be fatal if left untreated.

Synergism has also been noted in describing how complex systems operate. For example, biological systems may react in a non-linear way to perturbations, so that the outcome may be greater than the sum of the individual component alterations.

In describing the present invention, synergism means that the combination of the two active drugs, utilized in the methods and compositions of the invention achieves a result.

In accordance with the invention as described herein, there is provided a method for enhancing scalp hair growth in a mammal or animal in need thereof which comprises administering to the mammal an effective amount and, in some embodiments synergistically effective amounts, of 5 Beta dihydrotestosterone, androgen receptor blocker medications, bimatoprost other prostamides or minoxidil or hair growth promoting agents or therapies. Thus, in accordance with the present invention, synergistically effective amounts of 5 Beta dihydrotestosterone, androgen receptor blocker medications, bimatoprost other prostamides or minoxidil to stimulate the conversion of vellus hair to growth as terminal hair as well as increase the rate of growth of scalp terminal hair.

In said method of this invention, the concentration of added bimatoprost and/or minoxidil are administered as a composition comprising from 0.0000001% to 10% bimatoprost and from 0.001% to 10% minoxidil, by weight.

Some concentrations of minoxidil include from about 0.001 to about 5 to about 10% w/w, from about 0.005 to about 5, from about 0.01 to about 5, from about 0.05 to about 5, from about 0.1 to about 5, from about 0.5 to about 5, from about 1 to about 5, from about 1.5 to about 5, from about 2 to about 5, from about 2.5 to about 5, from about 3 to about 5, from about 3.5 to about 5, from about 4 to about 5, from about 4.5, from about 0.001 to about 4.5, from about 0.005 to about 4.5, from about 0.01 to about 4.5, from about 0.05 to about 4.5, from about 0.1 to about 4.5, from about 0.5 to about 4.5, from about 1 to about 4.5, from about 1.5 to about 4.5, from about 2 to about 4.5, from about 2.5 to about 4.5, from about 3 to about 4.5, from about 3.5 to about 4.5, from about 4 to about 4.5, from about 0.001 to about 4, from about 0.005 to about 4, from about 0.01 to about 4, from about 0.05 to about 4, from about 0.1 to about 4, from about 0.5 to about 4, from about 1 to about 4, from about 1.5 to about 4, from about 2 to about 4, from about 2.5 to about 4, from about 3 to about 4, from about 3.5 to about 4, from about 0.001 to about 3.5, from about 0.005 to about 3.5, from about 0.01 to about 3.5, from about 0.05 to about 3.5, from about 0.1 to about 3.5, from about 0.5 to about 3.5, from about 1 to about 3.5, from about 1.5 to about 3.5, from about 2 to about 3.5, from about 2.5 to about 3.5, from about 3 to about 3.5, from about 0.001 to about 3, from about 0.005 to about 3, from about 0.01 to about 3, from about 0.05 to about 3, from about 0.1 to about 3, from about 0.5 to about 3, from about 1 to about 3, from about 1.5 to about 3, from about 2 to about 3, from about 2.5 to about 3, from about 0.001 to about 2.5, from about 0.005 to about 2.5, from about 0.01 to about 2.5, from about 0.05 to about 2.5, from about 0.1 to about 2.5, from about 0.5 to about 2.5, from about 1 to about 2.5, from about 1.5 to about 2.5, from about 2 to about 2.5, from about 0.001 to about 2, from about 0.005 to about 2, from about 0.01 to about 2, from about 0.05 to about 2, from about 0.1 to about 2, from about 0.5 to about 2, from about 1 to about 2, from about 1.5 to about 2, from about 0.001 to about 1.5, from about 0.005 to about 1.5, from about 0.01 to about 1.5, from about 0.05 to about 1.5, from about 0.1 to about 1.5, from about 0.5 to about 1.5, from about 1 to about 1.5, from about 0.001 to about 1, from about 0.005 to about 1, from about 0.01 to about 1, from about 0.05 to about 1, from about 0.1 to about 1, from about 0.5 to about 1, from about 0.001 to about 0.5, from about 0.005 to about 0.5, from about 0.01 to about 0.5, from about 0.05 to about 0.5, from about 0.1 to about 0.5, from about 0.001 to about 0.1, from about 0.005 to about 0.1, from about 0.01 to about 0.1, from about 0.05 to about 0.1, from about 0.001 to about 0.05, from about 0.005 to about 0.05, from about 0.01 to about 0.05, or from about 0.001 to about 0.005% (w/w). In some embodiments, the minoxidil is present at about 0.001, 0.005, 0.01, 0.05, 0.1, 0.5, 1, 1.5, 2, 2.5, 3, 3.5, 4, 4.5, or 5% (w/w).

Minoxidil may also be present in 5.5% w/w to about 10% w/w, from about 6% w/w to about 10% w/w, from about 6.5% w/w to about 10% w/w, from about 7% w/w to about 10% w/w, from about 7.5% w/w to about 10% w/w, from about 8% w/w to about 10% w/w, from about 8.5% w/w to about 10% w/w, from about 9% w/w to about 10% w/w, from about 9.5% w/w to about 10% w/w, from about 5% w/w to about 9.5% w/w, 5.5% w/w to about 9.5% w/w, from about 6% w/w to about 9.5% w/w, from about 6.5% w/w to about 9.5% w/w, from about 7% w/w to about 9.5% w/w, from about 7.5% w/w to about 9.5% w/w, from about 8% w/w to about 9.5% w/w, from about 8.5% w/w to about 9.5% w/w, from about 9% w/w to about 9.5% w/w, from about 5% w/w to about 9% w/w, 5.5% w/w to about 9% w/w, from about 6% w/w to about 9% w/w, from about 6.5% w/w to about 9% w/w, from about 7% w/w to about 9% w/w, from about 7.5% w/w to about 9% w/w, from about 8% w/w to about 9% w/w, from about 8.5% w/w to about 9% w/w, from about 5% w/w to about 8.5% w/w, 5.5% w/w to about 8.5% w/w, from about 6% w/w to about 8.5% w/w, from about 6.5% w/w to about 8.5% w/w, from about 7% w/w to about 8.5% w/w, from about 7.5% w/w to about 8.5% w/w, from about 8% w/w to about 8.5% w/w, from about 5% w/w to about 8% w/w, 5.5% w/w to about 8% w/w, from about 6% w/w to about 8% w/w, from about 6.5% w/w to about 8% w/w, from about 7% w/w to about 8% w/w, from about 7.5% w/w to about 8% w/w, from about 5% w/w to about 7.5% w/w, 5.5% w/w to about 7.5% w/w, from about 6% w/w to about 7.5% w/w, from about 6.5% w/w to about 7.5% w/w, from about 7% w/w to about 7.5% w/w, from about 5% w/w to about 7% w/w, 5.5% w/w to about 7% w/w, from about 6% w/w to about 7% w/w, from about 6.5% w/w to about 7% w/w, from about 5% w/w to about 6.5% w/w, 5.5% w/w to about 6.5% w/w, or from about 6% w/w to about 6.5% w/w. In some embodiments, minoxidil is present at about 5, 5.5, 6, 6.5, 7, 7.5, 8, 8.5, 9, 9.5 or 10% (w/w).

In accordance with one aspect of the invention, the drugs 5 Beta dihydrotestosterone, 5 alpha reductase inhibitors, androgen receptor blocker medications, bimatoprost and/or minoxidil, are mixed with a dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of scalp hair growth, which comprise an effective scalp hair growth stimulating amount of 5 Beta dihydrotestosterone, other androgens, androgen receptor blocker medications, bimatoprost and/or minoxidil and a dermatologically compatible carrier. Effective amounts of the active compounds may be determined by one of ordinary skill in the art but will vary depending on the frequency of application and desired result, and bimatoprost will range from about 0.0000001 to about 10%, by weight, of the dermatological composition, preferably from about 0.001 to about 10%, by weight, of total dermatological composition, more preferably from about 0.03 to about 5%, by weight, of the composition and minoxidil will range from about 0.001 to about 10%, by weight, of the dermatological composition, preferably from about 0.01 to about 10%, by weight, of the composition.

EXAMPLES

5 Beta dihydrotestosterone (5-β-DHT) is prepared as a formulation in amounts effective in the methods of the disclosure. The formulation includes 5-β-DHT either as a monotherapy or in combination with other active agents. Amounts of 5-β-DHT, from about 0.1% to about 25%, depending on route and indication are incorporated into a base foamable liquid composition. As a combination formulation, 5-β-DHT is formulated into a foamable liquid composition containing approximately 0.03% by weight bimatoprost and 5%, by weight minoxidil is prepared by dissolving the bimatoprost and minoxidil in an alcohol-containing solvent. Said foamable liquid composition further includes a solvent system, a surfactant and a foam stabilizer. The solvent system, includes water, an alcohol and, optionally, an acid and a water soluble solvent. This composition is prepared by methods known in the art. A method of delivering a foam product according to the present invention comprises the following steps: providing a foamable liquid composition comprising 5 percent, by weight, minoxidil and 0.03 percent, by weight, bimatoprost or a pharmaceutically acceptable salt of either or both of minoxidil or bimatoprost, in an amount or amounts sufficient to provide: 5 percent, by weight, minoxidil, and 0.03 percent, by weight, bimatoprost in a container adapted for dispensing the foamable liquid composition as a foam and dispensing the foamable liquid composition as a foam from said container onto the skin of a patient. Alternatively, minoxidil may be used in an amount of from 0.5 to 10 percent and preferably in an amount of from 2 to 5 percent, by weight, relative to the total weight of the foamable liquid composition. Bimatoprost may be used in an amount of from 0.01 to 3 percent and more preferably in an amount of from 0.03 to 1 percent, by weight, relative to the total weight of the liquid composition. The solvent system is an aqueous-alcoholic medium, which enables solubilization of minoxidil and bimatoprost. In one example, the foamable liquid composition includes from 30 to 80 percent water, by weight. Preferably the foamable liquid composition comprises from 30 to 60 percent water, by weight.

Preferably, the foamable liquid composition further includes an acid at a concentration of from 0.5 to 5 percent, by weight, of the foamable liquid composition. The acid may be selected from the group consisting of an inorganic acid, an organic acid with chain length of eight carbons or less and mixtures thereof. A preferred foamable liquid composition includes from 1 to 4 percent, by weight, lactic acid, from 1 to 50, preferably from 5 to 30 percent, by weight, of an alcohol having from one to four carbon atoms, such as methanol, ethanol, propanol and mixtures thereof, and one or more water soluble solvents, such as butylene glycol, glycerin, polyglycerin, ethylene glycol, and propylene glycol. Preferably, said alcohol is ethanol and preferably said water soluble solvent is propylene glycol in an amount of from 1 to 20 percent, by weight, and more preferably from 5 to 15 percent, by weight, of the foamable liquid composition. The liquid foam composition according to the invention contains at least one surfactant. Preferably, the foamable liquid composition comprises from 0.1 to 5 percent, by weight, of a surfactant, more preferably from 0.2 to 1 percent, by weight of a surfactant. Suitable surfactants have emulsifying, solvating, and foam-forming or foam-stabilizing properties; are preferably nonionic; and have a hydrophilic-lipophilic balance (HLB) value of greater than about fifteen. In particular, the surfactant oleth-20 is preferred in an amount of from 0.1 to 5 percent, by weight, of the foamable liquid composition and more preferably from 0.2 to 1 percent, by weight, of the foamable liquid composition.

Other surfactants optionally used with the present formulation include, but are not limited to: any combination of anionic, cationic, non-ionic, or amphoteric surfactants with an HLB value of greater than fifteen.

Optionally, the foam formed is maintained with a foam stabilizer. In the treatment of the human scalp for androgenic alopecia the maintenance of foam is important to allow a known and suitable period of contact of the agents (5-β-DHT alone or in combination with minoxidil and bimatoprost) with the scalp.

The foam stabilizer is preferably included in the foamable liquid composition in an amount of from 0.05 to 0.5 percent, and more preferably from 0.1 to 0.5 percent, by weight.

In particular, the stabilizer includes lauryl glucoside in an amount of from 0.05 and 0.5% by weight and more preferably from 0.1 to 0.5 percent, by weight, of the foamable liquid composition.

Other optional foam stabilizers used with the present liquid composition include, but are not limited to: fatty amine oxides, a quaternary amines, or a cellulose derivatives, such as methyl cellulose and ethyl cellulose.

The liquid composition can be sprayed on the scalp daily to stimulate the growth of hair, based on dosages effective to stimulate hair growth.

What is claimed is:

1. A method for promoting and enhancing hair growth in a human in need thereof, comprising applying a topical formulation of 5 Beta dihydrotestosterone, or a salt or pharmaceutically acceptable carrier or formulation thereof, to the skin of the human.

2. The method of claim 1, wherein the method comprises administering to the subject 5 Beta Dihydrotestosterone (5β-DHT) (17β-hydroxy-5β-androstan-3-one) a topical liquid, lotion, ointment, solution, gel, foam, or spray.

3. The method of claim 1, wherein the method comprises administration that is effective to promote hair growth on the scalp of the subject.

* * * * *